US011902743B2

(12) United States Patent
Vanpoucke

(10) Patent No.: US 11,902,743 B2
(45) Date of Patent: *Feb. 13, 2024

(54) NORMALIZATION FITTING METHOD

(71) Applicant: Cochlear Limited, Macquarie University (AU)

(72) Inventor: Filiep J. Vanpoucke, Mechelen (BE)

(73) Assignee: Cochlear Limited, Macquarie University (AU)

(*) Notice: Subject to any disclaimer, the term of this patent is extended or adjusted under 35 U.S.C. 154(b) by 277 days.

This patent is subject to a terminal disclaimer.

(21) Appl. No.: 16/995,211

(22) Filed: Aug. 17, 2020

(65) Prior Publication Data

US 2022/0053272 A1    Feb. 17, 2022

Related U.S. Application Data

(63) Continuation of application No. 15/009,183, filed on Jan. 28, 2016, now Pat. No. 10,750,301.

(60) Provisional application No. 62/160,758, filed on May 13, 2015.

(51) Int. Cl.
H04R 25/00    (2006.01)

(52) U.S. Cl.
CPC .......... *H04R 25/30* (2013.01); *H04R 25/356* (2013.01)

(58) Field of Classification Search
CPC .............................. H04R 25/30; H04R 25/356
See application file for complete search history.

(56) References Cited

U.S. PATENT DOCUMENTS

| | | | |
|---|---|---|---|
| 2007/0135862 A1* | 6/2007 | Nicolai | A61N 1/36039 607/56 |
| 2010/0041940 A1* | 2/2010 | Hillbratt | H04R 25/606 600/25 |
| 2010/0145411 A1* | 6/2010 | Spitzer | A61N 1/36039 607/57 |
| 2014/0211971 A1* | 7/2014 | Sohn | H04R 25/70 381/312 |

OTHER PUBLICATIONS

Robinson, Threshold of Hearing and Equal-Loudness Relations for Pure Tones, and the Loudness Function, 1957, The Journal of the Acoustical Society of America, whole document (Year: 1957).*
Bauer, Researches in Loudness Measurements, 1966, IEEE Transactions on Audio and Acoustics. whole document (Year: 1966).*

* cited by examiner

*Primary Examiner* — Sonia L Gay
(74) *Attorney, Agent, or Firm* — Piloff Passino & Cosenza LLP; Martin J. Cosenza

(57) ABSTRACT

A method, including obtaining data indicative of respective perceived loudness levels for a plurality of hearing percepts respectively evoked at different current levels, and creating a map for the hearing prosthesis based on the obtained data by adjusting at least one of the respective current levels based on data of a respective perceived loudness for another current level.

26 Claims, 15 Drawing Sheets

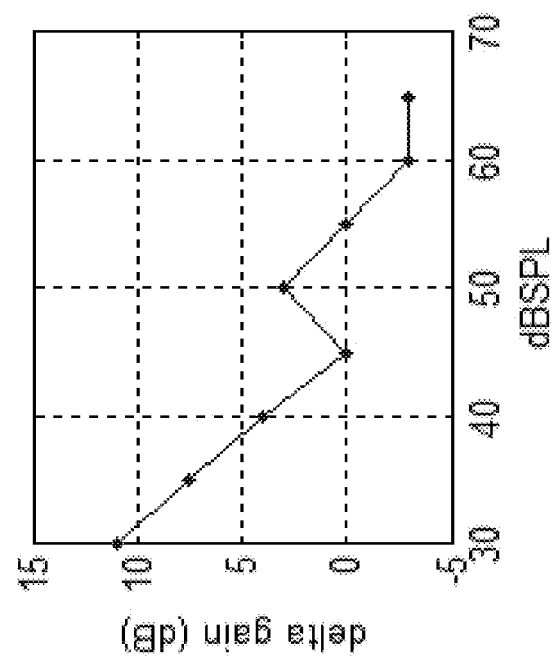

NORMALIZATION FITTING METHOD

CROSS-REFERENCE TO RELATED APPLICATIONS

This application is a Continuation application of U.S. patent application Ser. No. 15/009,183, filed Jan. 28, 2016, which claims priority to Provisional U.S. Patent Application No. 62/160,758, entitled NORMALIZATION FITTING METHOD, filed on May 13, 2015, naming Filiep J. VAN-POUCKE of Belgium as an inventor, the entire contents of each application being incorporated herein by reference in their entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

It is noted that in at least some instances, there is utilitarian value to fitting a hearing prosthesis to a particular recipient. In some examples of some fitting regimes, there are methods which entail a clinician or some other professional presenting sounds to a recipient of the hearing prosthesis such that the hearing prosthesis evokes a hearing percept. Information can be obtained from the recipient regarding the character of the resulting hearing percept. Based on this information, the clinician can adjust or otherwise establish settings of the hearing prosthesis such that the hearing prosthesis operates according to these settings during normal use.

SUMMARY

In accordance with an exemplary embodiment, there is a method, comprising obtaining data indicative of respective perceived loudness levels for a plurality of hearing percepts respectively evoked at different current levels, and creating a map for the hearing prosthesis based on the obtained data by adjusting at least one of the respective current levels based on data of a respective perceived loudness for another current level.

In accordance with another exemplary embodiment, there is a method comprising, obtaining data indicative of respective perceived loudness levels for a plurality of hearing percepts respectively evoked based on respective different stimulus having respective first different loudness levels, wherein the respective evoked hearing percepts are evoked with respective different energy outputs of a hearing prosthesis, obtaining data indicative of normalized loudness levels for normal hearers for the respective different stimulus having respective different first loudness levels, and configuring the hearing prosthesis to automatically evoke hearing percepts, in response to sound captured by the hearing prosthesis having respective second different loudness levels corresponding to the respective first different loudness levels, at respective new different energy levels different from those used to evoke the respective hearing percepts, for respective new respective stimulus having the respective first different loudness levels, based on the obtained data indicative of normalized loudness levels.

In accordance with another exemplary embodiment, there is a fitting system, comprising a sub-system configured to obtain statistical perceived loudness data, a sub-system configured to obtain hearing prosthesis recipient-specific loudness data for a plurality of different stimulus having at least some loudness levels corresponding to those of the statistical perceived loudness data, and a sub-system configured to automatically configure a hearing prosthesis based on the obtained statistical data and the obtained recipient-specific loudness data.

BRIEF DESCRIPTION OF THE DRAWINGS

Embodiments are described below with reference to the attached drawings, in which:

FIG. 8B presents an exemplary gain change chart for a range of loudness levels in an exemplary scenario in which the teachings detailed herein are utilized;

DETAILED DESCRIPTION

Figure 1:
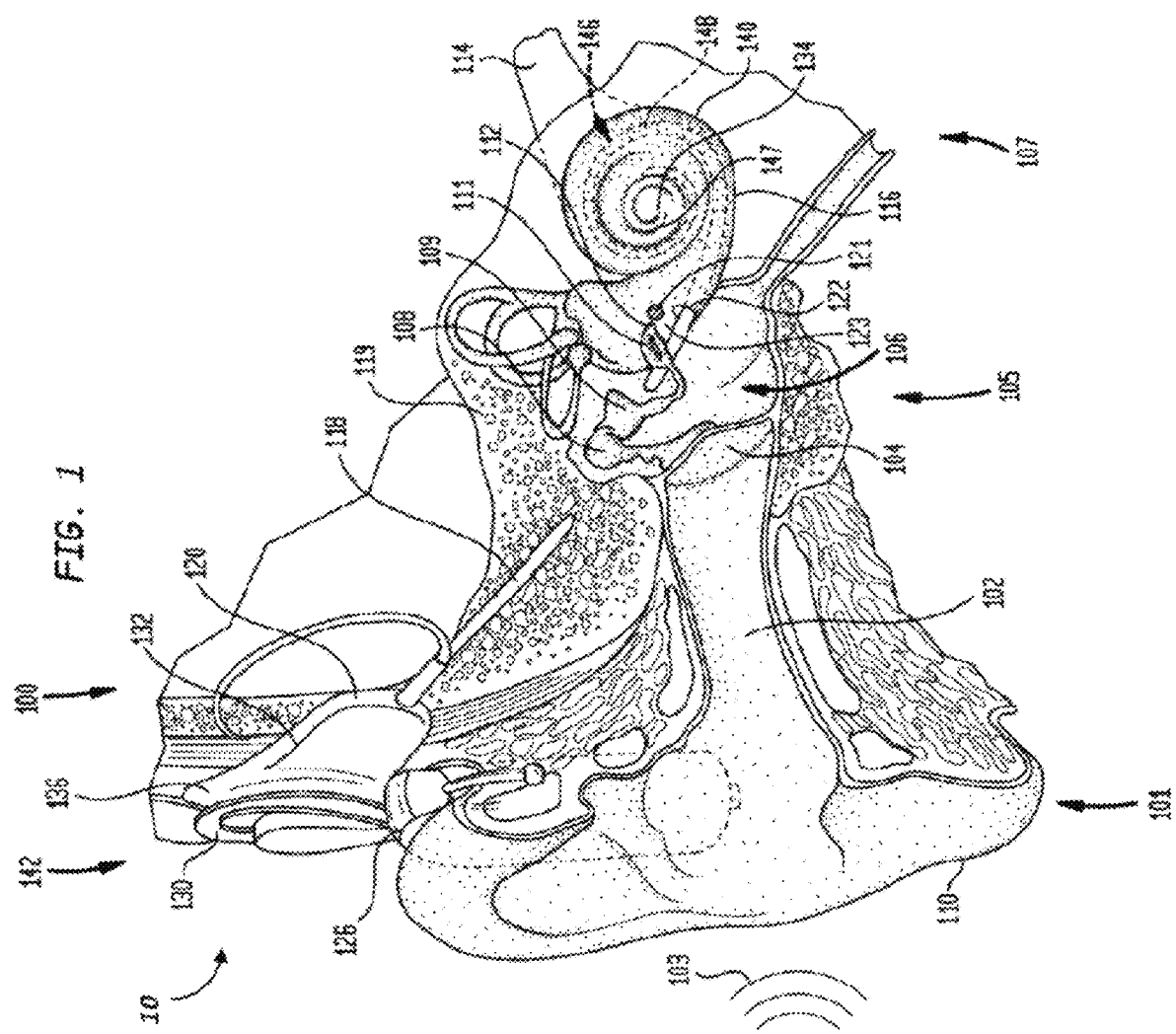
FIG. 1 is a perspective view of an exemplary hearing prosthesis in which at least some of the teachings detailed herein are applicable.

FIG. 1 is a perspective view of a cochlear implant, referred to as cochlear implant 100, implanted in a recipient, to which some embodiments detailed herein and/or variations thereof are applicable. The cochlear implant 100 is part of a system 10 that can include external components, in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.).

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery or other energy storage device (e.g., capacitor) that is charged (e.g., recharged) by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand/or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand/or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Because the cochlea is tonotopically mapped (i.e., spatial locations that are responsive to stimulus signals in a particular frequency range are identified), frequencies may be allocated to one or more electrodes of the electrode assembly to generate an electric field in positions in the cochlea that are close to the region that would naturally be stimulated in normal hearing. This enables the prosthetic hearing implant to bypass the hair cells in the cochlea to directly deliver electrical stimulation to auditory nerve fibers, thereby allowing the brain to perceive hearing sensations resembling natural hearing sensations. In achieving this, processing channels of the sound processing unit of the BTE 126 (i.e., specific frequency bands with their associated signal processing paths), are mapped to a set of one or more electrodes to stimulate a desired nerve fiber or nerve region of the cochlea. Such sets of one or more electrodes for use in stimulation are referred to herein as "electrode channels" or "stimulation channels." In at least some exemplary embodiments, each channel has a "base" electrode corresponding to the electrode of the electrode array that is proximate the tonotopically mapped cochlea for a given frequency or frequency range.

Figure 2:
FIG. 2 presents an exemplary electrode array according to an exemplary embodiment.

FIG. 2 illustrates a more detailed view, albeit functionally, of an exemplary electrode array 146 comprising a plurality of electrodes 148 labeled 1-22, in accordance with an embodiment. In an exemplary embodiment, each electrode 148 is an electrode that corresponds to a specific frequency band channel of the cochlear implant 100, where electrode 22 corresponds to the lowest frequency band (channel), and electrode 1 corresponds to the highest frequency band (channel), as will be discussed in greater detail below. Briefly, it is noted that during stimulation by the electrodes to evoke a hearing percept, one or more electrodes 148 is activated at a given electrode stimulation level (e.g., current level). This electrode stimulation level is pre-set during a fitting process. For example, in at least some instances, an audiologist adjusts stimulation channel electrode current levels of the cochlear implant 100 based on empirical data. More specifically, in at least some embodiments, stimulation channel electrode current levels are adjusted by an audiologist based on threshold and comfort levels. Then, in at least some embodiments, the cochlear implant 100 is configured such that respective stimulation channels of the cochlear implant 100 have those respective current levels. This can be done, for example, by programming the cochlear implant 100 or by any other process that sets the channels of the cochlear implant 100 to have the pertinent electrical stimulation levels. Any arrangement of the cochlear implant 100 and/or other equipment/devices that will enable the teachings detailed herein and/or variations thereof to be practiced can be used in at least some embodiments.

In view of this, an exemplary embodiment entails a fitting method that entails setting or otherwise adjusting the parameters of the cochlear implant 100 determining the electrical mapping from sound levels in one or more or all of the frequency bands to electrical stimulation levels. This exemplary fitting method can include an audiologist or other clinical professional tuning the electrical map parameters of the cochlear implant 100 to the particular auditory physiology of the recipient. More specifically, in at least some exemplary embodiments, as will be detailed below, the fitting methods detailed herein are directed towards obtaining a convergence between a perceived loudness, and a loudness corresponding to that of normal hearing people for a given stimulus and/or for a range of stimuli.

Figure 3:
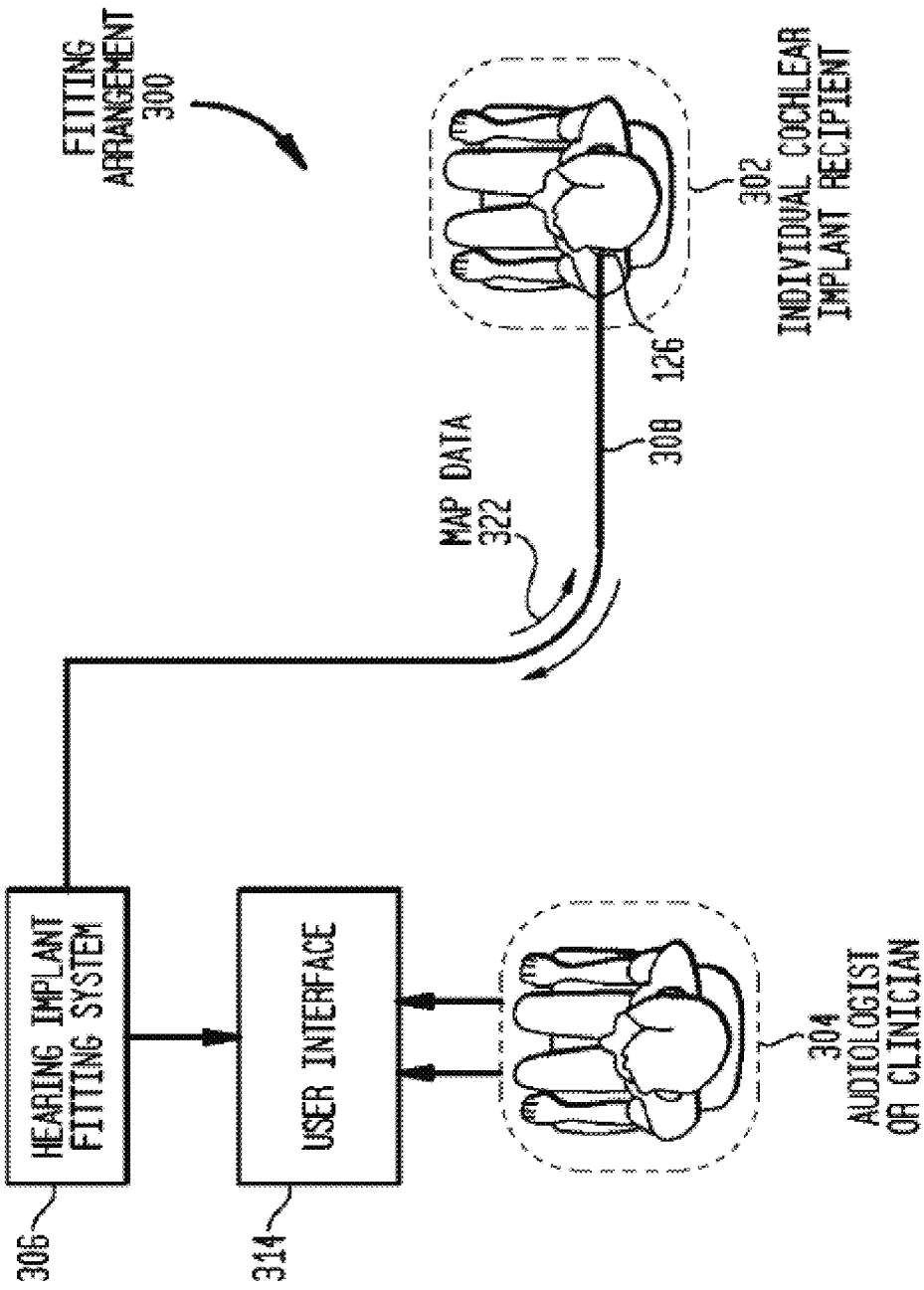
FIG. 3 presents an exemplary device in use according to an exemplary embodiment.

FIG. 3 is a schematic diagram illustrating one exemplary arrangement 300 in which a hearing implant fitting system 306 may be used to fit a cochlear implant, in accordance with an embodiment. As shown in FIG. 3, an audiologist or clinician 304 may use a hearing implant fitting system 306 ("fitting system" herein) comprising interactive software and computer hardware to create individualized recipient map data 322 that are digitally stored on system 306, and ultimately downloaded to the memory of the sound processing unit 126 for recipient 302. System 306 may be programmed and/or implement software programmed to carry out one or more of the functions of mapping, neural response measuring, acoustic stimulating, and recording of neural response measurements and other stimuli.

In the embodiment illustrated in FIG. 3, sound processing unit 126 of cochlear implant 100 may be connected directly to fitting system 306 to establish a data communication link 308 between the sound processing unit 126 and fitting system 306. System 306 is thereafter bi-directionally coupled by a data communication link 308 with sound processing unit 126. It should be appreciated that although sound processing unit 126 and fitting system 306 are connected via a cable in FIG. 3, any communications link now or later developed may be utilized to communicably couple the implant and fitting system.

Some exemplary embodiments will now be described in terms of utilizing the aforementioned fitting system 306 to fit the aforementioned cochlear implant 100 to achieve the aforementioned normalization convergence. It is noted that the following is but exemplary, and that alternative methods can be practiced utilizing other devices other than the fitting system 306 and/or alternative methods can be practiced to fit a prosthesis that is different than cochlear implant 100.

Briefly, at least some teachings detailed herein and/or variations thereof are applicable to the development of a map for a unilateral cochlear implant user that restores the loudness percept or otherwise adjust the loudness percept of a hearing percept evoked by the cochlear implant towards a value that is closer to that of a normal hearing person. As will be detailed herein, the teachings detailed herein and/or variations thereof can be applicable to other types of hearing prostheses other than a cochlear implant. Still further, the teachings detailed herein and/or variations thereof can be applicable in at least some embodiments to hybrid devices and bimodal devices that utilize the cochlear implant along with another type of hearing device (e.g., a traditional hearing aid).

More specifically, in at least some exemplary embodiments, there is an algorithm that enables the development, including the automatic development, of a new electrical output map such that the loudness ratings of the cochlear implant recipient are normalized (when the new map is utilized to evoke new hearing percepts). In at least some exemplary embodiments, the aforementioned loudness is normalized to values within the 95% confidence interval in a single step. By way of example only and not by way of limitation, a loudness scaling test (more on this below) need only be administered one time to develop a new electrical output regime that will result in the hearing percept that will more closely resemble that of the normal hearing person, and not multiple times (although the single test may include repeated providing of tones at a specific loudness for a specific frequency, as detailed below).

In an exemplary embodiment, a diagnostic loudness scaling test is performed on a recipient of the cochlear implant 100, which diagnostic loudness scaling test can be executed utilizing the fitting system 306 and/or another system. An exemplary embodiment utilizes the Adaptive Categorical Loudness Scaling test (ACALOS). Any loudness test that will enable the teachings detailed herein and/or variations thereof to be practiced can be utilized in at least some embodiments.

More specifically, in an exemplary embodiment, a recipient of the cochlear implant 100 having an initial electrode current level regime/embryonic map is subjected to multiple sound presentations corresponding to a plurality of different sound stimuli, typically discrete and temporally segregated from one another, respectively having different respective loudness levels (and thus the recipient is exposed to multiple sound presentation levels). The cochlear implant 100 evokes respective hearing percepts (or attempts to evoke such—sometimes a hearing percept cannot be evoked because the given sound stimuli is below a threshold level) utilizing the initial electrode charge level regime/embryonic map thereof. The recipient indicates his or her perception of loudness of each resulting hearing percept. By way of example only and not by way of limitation, in an exemplary embodiment, a plurality of noise bands are presented to the recipient of the hearing prosthesis at multiple presentation levels, ranging from 30 to 80 dBSPL, in steps of 5 dB, although the range can be different than this (e.g., 20 to 100 dBSPL, 25 to 75 dBSPL, any value or range of values that can enable the teachings detailed herein and/or variations thereof) and/or the increments can be different than this (e.g., increments of 2.5 dB, 7.5 dB, 10 dB, etc.). Any value or range of values in any increment that can enable the teachings detailed herein and/or variations thereof can be utilized in at least some embodiments.

In an exemplary embodiment, the various presentation levels are randomly selected and randomly presented to the recipient. In alternative embodiments, the various presentation levels are presented in an ascending and/or a descending order. As will be detailed herein, in an exemplary embodiment includes a device and/or a system that automatically provides the various presentation levels to the recipient.

In an exemplary embodiment, each stimuli is presented twice or three or four or five or more times (i.e., each presentation level is presented twice), and the results (i.e., the perceived respective loudness levels) are averaged. That said, in an alternative embodiment, each stimulus is only presented once. The results of the various presentations are compiled into a loudness growth function, in at least some exemplary embodiments, the scaling test is repeated for 2 or more frequency regions (e.g., for every octave, for 250 Hz, 1000 Hz and 4000 Hz, etc.).

Figure 4:
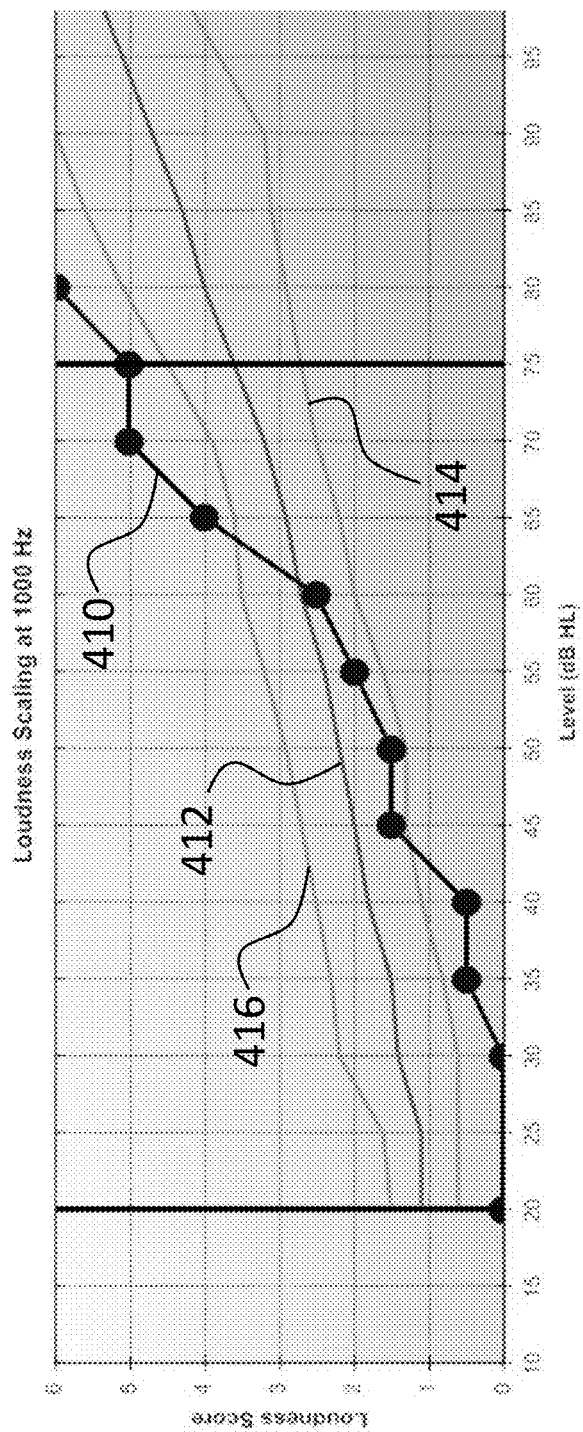
FIG. 4 presents exemplary loudness scaling tests results along with statistical loudness data.

FIG. 4 presents an exemplary chart presenting results of an exemplary scaling test for tones presented at 1000 Hz (the tones were presented twice, and the averaged loudness score was averaged). In this regard, curve 410 constitutes empirical results from the scaling test, where stimuli level (dBHL) is correlated to indicated loudness score on a scale of 0-6, with 0 being non-audible, 1 being very soft, 2 being soft, 3 being normal sounding, 4 being loud, 5 being very loud and 6 being too loud. Each circle represents an empirical data point, and the solid lines connecting each circle represent linear interpolation curve fitting. It is noted that in an alternative embodiment, other curve fitting techniques can be utilized, including those that do not necessarily result in curves that pass through each specific empirical data point. Any curve fitting technique that can enable the teachings detailed herein and/or variations thereof can be utilized in at least some embodiments. Further, consistent with the description above, while 5 dB increments have been utilized over a range of 20 dBHL to 80 dBHL, other increments and/or other ranges could have been utilized to generate the curve 410.

The solid the black vertical lines at 20 dBHL and 75 dBHL in FIG. 4 represents sound levels beyond which distinguishing loudness/softness is not deemed utilitarian in this exemplary embodiment.

FIG. 4 contains three additional curves beyond 410: curve 412, curve 414 and curve 416. Curve 412 entails statistical data corresponding to the fiftieth percentile normal hearing person. That is, in an exemplary embodiment, based on a statistically significant group of representative normal hearers (e.g., those that do not utilize a hearing prosthesis to hear), a mean, median and/or modal average of normal hearers would rate a given loudness level according to that presented along the curve 412. Curve 414 corresponds to a curve that relates to a statistically significant group of representative normal hearers, where 97.5 percent of such people rate the given loudness level as a value at or above that curve. Conversely, curve 416 corresponds to a curve that relates to a statistically significant group of representative normal hearers, where 97.5 percent of such people rate the given loudness level as a value at or below that curve, the difference between curve 414 and curve 416 being that the people represented by curve 414 perceived the given loudness levels as softer than the average normal hearer, and the people represented by curve 416 perceived the given loudness levels as louder than the average normal hearer. Put another way, according to the exemplary embodiment, 95% of normal hearing people will rate a given loudness level as having a value between and on curves 414 and 416. Other statistical populations can be utilized (e.g., the curves 414 and 416 can correspond to curves that relate to a statistically significant group of representative normal hearers, where 90% of such people rate the given loudness level as a value above the curve/below the curve, 99% of such people rate the given loudness level as a value above the curve/below the curve etc.). In this regard, the curves 414 and 416 represent statistical confidence intervals associated with the statistical average data. Tighter or looser confidence margins can be utilized depending on a particular embodiment. In this regard, curves 414 and 416 represent a 95% confidence interval.

An exemplary embodiment entails utilizing the empirical curve 410 (or, more generally, the empirical data associated with the empirical curve 410) in combination with one or more of the statistical curves 412, 414 or 416 (or, more generally, the statistical data associated with the statistical curves) to adjust or otherwise change the initial electrode charge level regime/embryonic map of the cochlear implant 100 utilized to develop the empirical curve 410 (the empirical data associated therewith) such that the resulting hearing percepts will have loudness values more in line with those statistical curves (statistical data).

Figure 5:
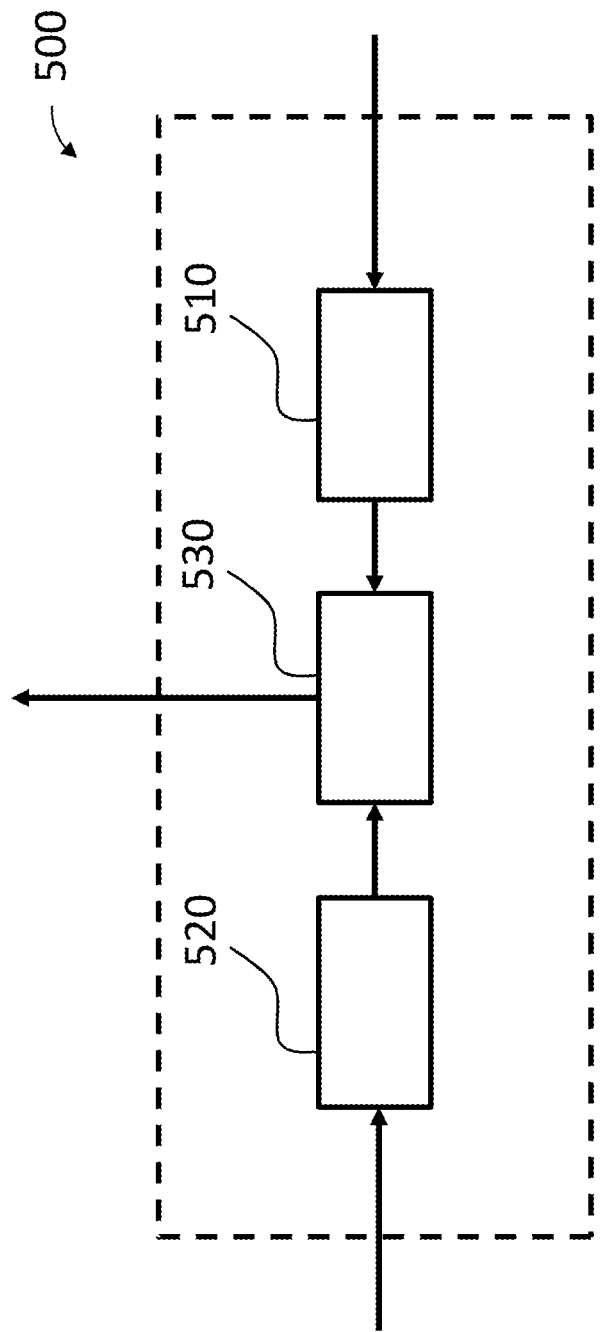
FIG. 5 presents, by way of a functional schematic, an exemplary system according to an exemplary embodiment.

Thus, briefly, with reference to FIG. 5, in an exemplary embodiment, fitting system 306 can be functionally characterized as a system 500, comprising a subsystem 510 configured to obtain recipient-specific loudness data (as represented by the arrow pointing towards black box 510) for a plurality of different stimuli having at least some loudness levels corresponding to those of the statistical perceived loudness data, a subsystem 520 configured to obtain statistical perceived loudness data (as represented by the arrow pointing towards black box 520, and a subsystem 530 configured to automatically configure a hearing prosthesis (as represented by the arrow pointing away from black box 530) based on the obtained statistical data and the obtained recipient-specific loudness data (as represented by the arrows respectively pointing from black boxes 510 and 520 to black box 530).

In an exemplary embodiment, system 500 can be a personal computer, a laptop computer, a mainframe computer, a network and/or units connected by a network (as represented by the dashed lines—each component of the system 500 can be located at separate remote facilities), or a portable computing device (e.g., a smartphone having sufficient computational power), in which case, in some embodiments, system 500 can correspond to both fitting system 306 and user interface 312 with respect to FIG. 3. System 500 can alternatively be a portion of one or more of the aforementioned devices. In an exemplary embodiment, subsystem 510 can obtain the recipient specific loudness data as a result of the system 500 having the functionality to administer the aforementioned scaling test. In an exemplary embodiment, this can be done autonomously in an interactive manner with the recipient without a clinician operating the machine. Alternatively and/or in addition to this, the system 500 can be operated by a clinician. Alternatively and/or in addition to this, subsystem 510 can obtain the recipient specific loudness data as a result of data being uploaded to the system 500 (e.g., the subsystem 510 can obtain the loudness data via a USB communication or the like and/or via an ethernet connection or the like and/or via an optical media data storage device etc.). In this regard, unless otherwise specified, as utilized herein, the phrase "obtaining data" encompasses both the action of performing an empirical test to develop the data as well as the action of obtaining data indicative of a prior test without actually executing the empirical test.

In an exemplary embodiment, subsystem 520 can obtain the statistical perceived loudness data as a result of data being uploaded (e.g., the subsystem 520 can obtain the statistical data via a USB communication or the like, and/or via an ethernet connection or the like, and/or via an optical media data storage device, etc.).

Any device, system, and/or method that will enable the statistical data and/or the recipient specific loudness data to be obtained by the system, can be utilized in at least some embodiments, providing that the teachings detailed herein and/or variations thereof can be practiced utilizing such.

Subsystem 530 is configured to receive data from subsystem 510 and 520 and to automatically configure the cochlear implant 100 based on the obtained statistical data and the obtained recipient-specific loudness data via the use of an exemplary algorithm as detailed below and/or via other types of algorithms. In an exemplary embodiment, subsystem 530 is a CPU of a personal computer, or a processor of a portable computing device, or a processor linked to the subsystems 510 and 520 via a network (e.g., internet, etc.). In an exemplary embodiment, subsystem 530 utilizes an algorithm to develop a map based on the data from subsystem 510 and 520 that will enable the recipient to perceive hearing percepts at a loudness closer to that of the normal hearing recipient relative to that which was the case utilizing the embryonic map/initial electrode current regime used to develop the data obtained by the first subsystem 510.

Some exemplary methods and algorithms usable with the system 500 and/or usable aside from the system 500 will now be described.

Figure 6:
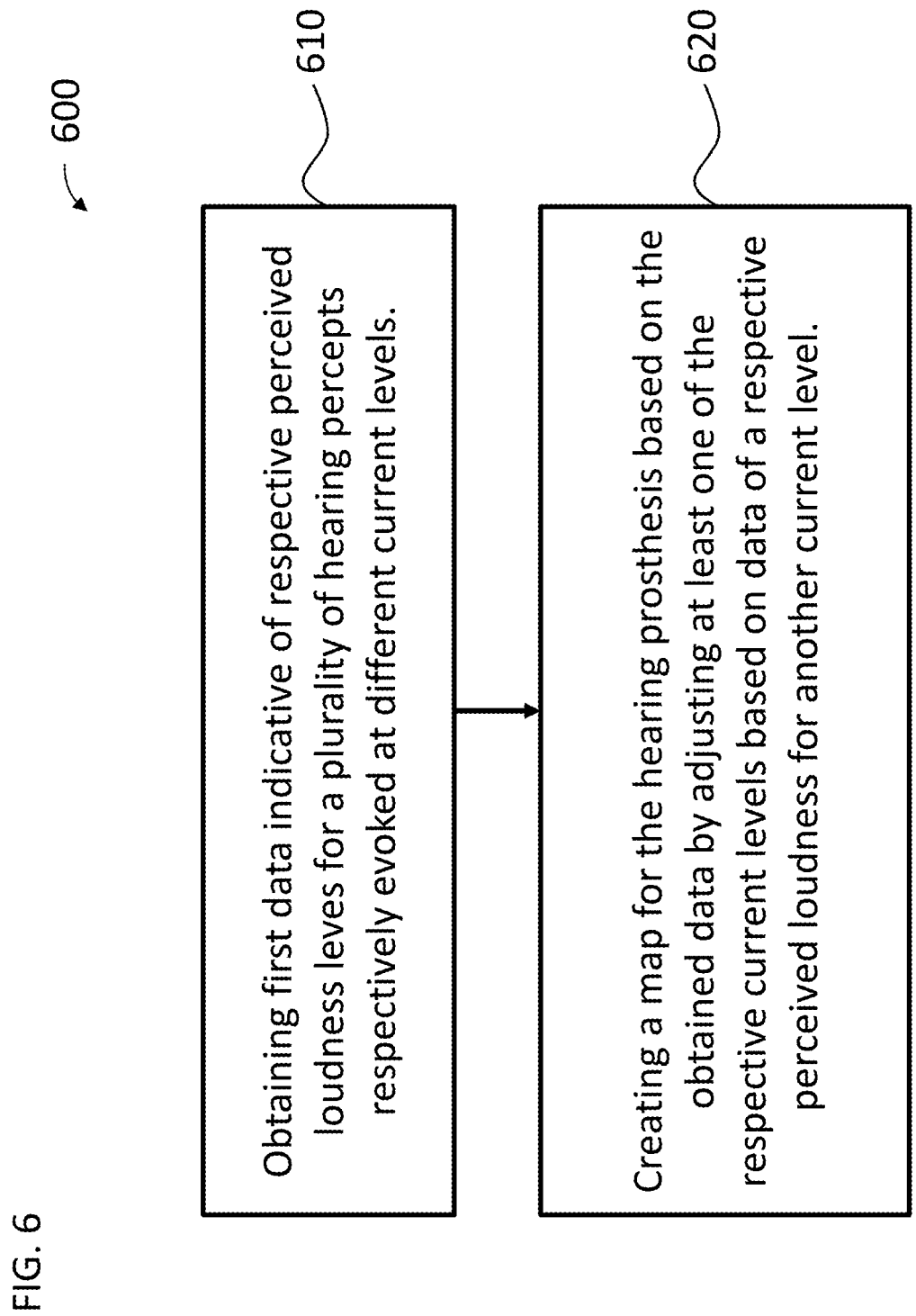
FIG. 6 presents a flowchart according to an exemplary embodiment.

FIG. 6 presents a flowchart 600 containing an exemplary algorithm for an exemplary method. Flowchart 600 includes action 610, which entails obtaining data indicative of respective perceived loudness levels for a plurality of hearing percepts respectively evoked at different current levels. In an exemplary embodiment, this entails subjecting the recipient of a cochlear implant 100 to the scaling test detailed above, where the different current levels correspond to a phenomenon associated with the cochlear implant 100 where increased current level is correlated to increased perceived loudness of the different stimuli upon which the hearing percepts are based. With respect to FIG. 4, increased loudness levels correspond to the utilization of increased current levels to evoke the respective hearing percepts, at least according to the exemplary embryonic map utilized to evoke those hearing percepts for the scaling test. It is also noted that while in at least some embodiments, method action 610 is accomplished by subjecting the recipient to the scaling test noted above, in an alternate embodiment, method action 610 is accomplished by obtaining the data compiled as a result of the scaling test. That is, the actual scaling test need not be executed as part of method action 610 (e.g., the scaling test can be executed prior to the execution of method action 610). Accordingly, it is not necessary to directly conduct the scaling test to execute method action 610. Simply obtaining the data from the source that obtain the data (either directly or indirectly (e.g., from another source)) via scaling test is sufficient to execute method action 610 in at least some embodiments.

Figure 7:
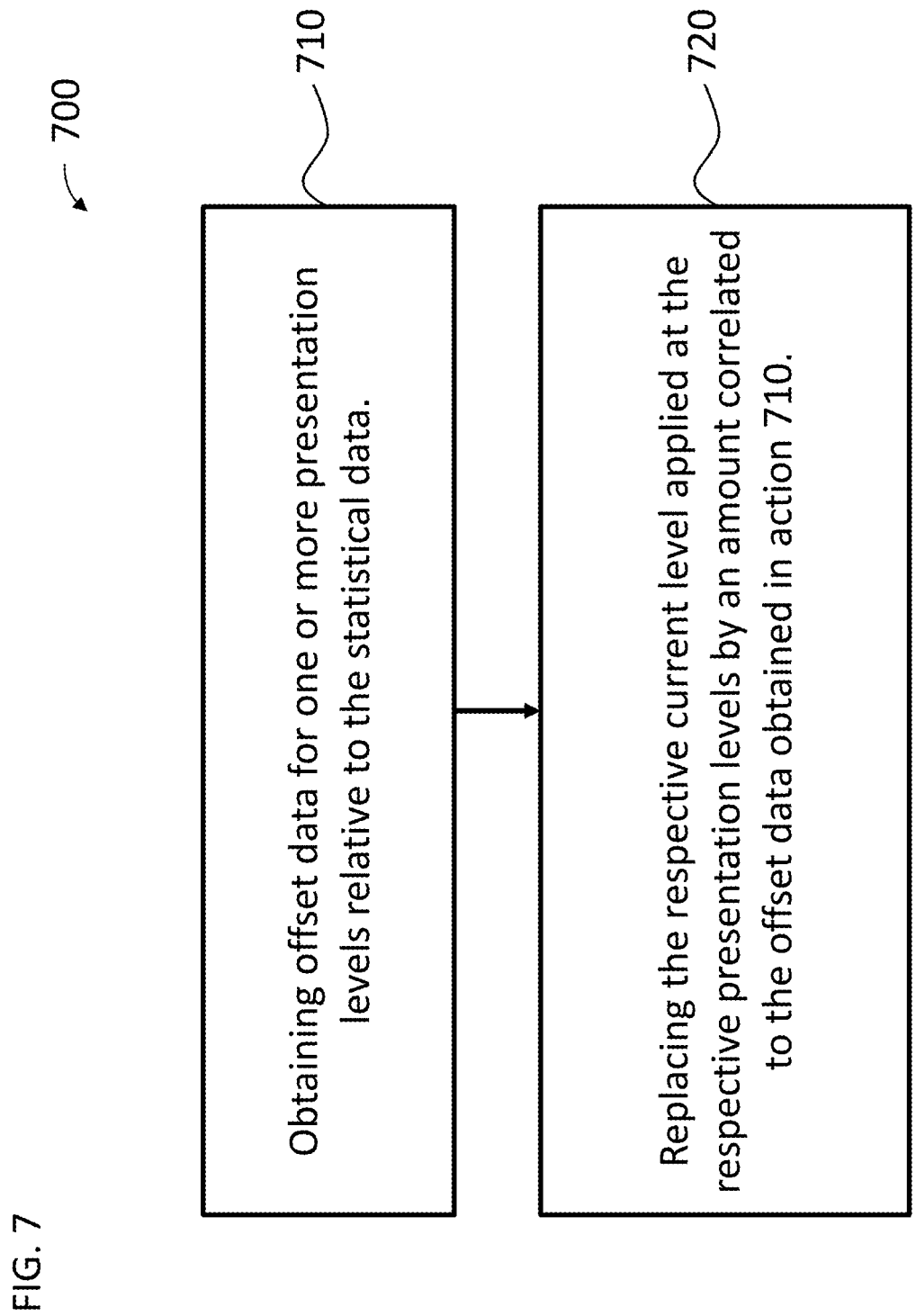
FIG. 7 presents another flowchart according to another exemplary embodiment.
Figure 8A:
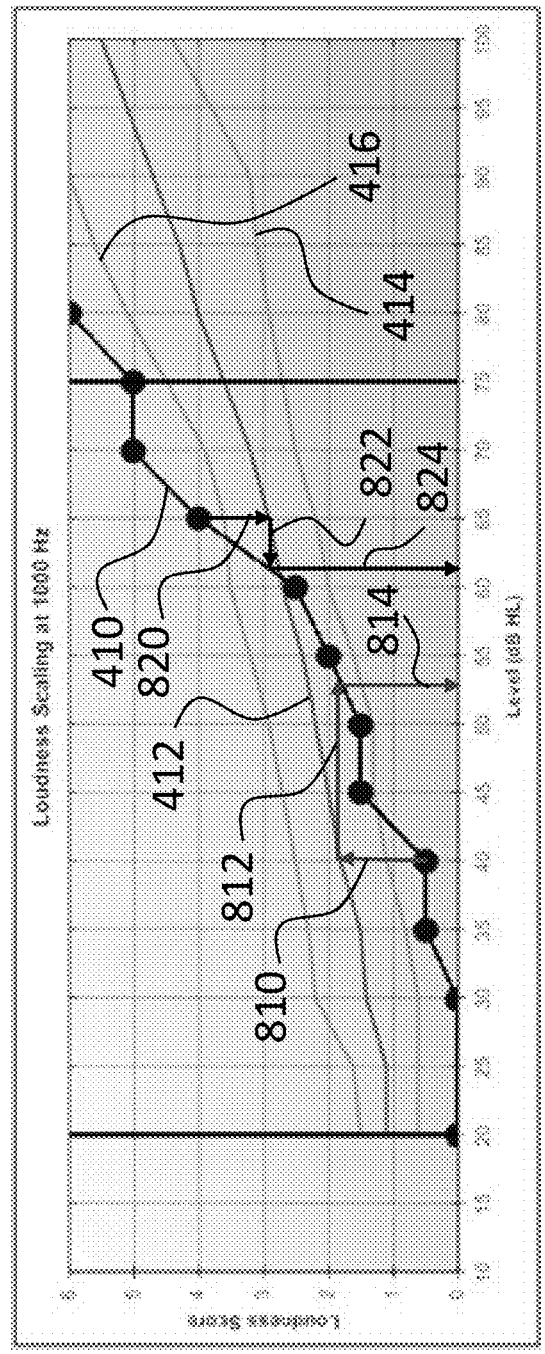
FIG. 8A presents exemplary loudness scaling tests results along with statistical loudness data along with graphical symbols conveying a high-level concept of an exemplary method of normalizing loudness with a hearing prosthesis.

After method action 610 is executed, flow chart 600 proceeds to method action 620, which entails creating a map (e.g., a new map) for the hearing prosthesis based on the obtained data obtained in method action 610 by adjusting at least one of the respective current levels based on data of a respective perceived loudness correlated to another current level different from the respective current level. More specifically, in an exemplary embodiment, method action 620 can be executed via the algorithm represented by flowchart 700 of FIG. 7. Flowchart 700 includes method action 710, which entails obtaining offset data from one or more presentation levels relative to the statistical data (i.e., the normal hearing data, such as curve 410 of FIG. 4). FIG. 8A schematically illustrates method action 710 with respect to the presentation level associated with 40 dBHL and the presentation level associated with 65 dBHL. More specifically, with respect to the loudness reading at the presentation level of 40 dB, the recipient indicated that the perceived loudness of the hearing percept evoked by that stimulus was below very, very soft (0.5 on the chart, between 0 and 1). Conversely, the average normal hearing person would have perceived the loudness level of the stimuli (the sound at 40 dBHL) as being about soft (almost level 2 on the chart). The difference between these two data points is represented by the vertical arrow 810 extending from the empirical data point at 40 dBHL. In an exemplary algorithm, the empirical curve 410 is utilized in method action 710 to obtain a loudness level corresponding to that which the recipient would rate the same as, or at least approximately the same as, that of the normal hearing person. With regard to the exemplary empirical curve 410 of FIG. 8, this corresponds to a loudness level of 52 dBHL, as is represented by the horizontal arrow 812 extending from the aforementioned vertical arrow 810, and the downwardly pointing vertical arrow 814 extending from the horizontal arrow.

FIG. 8A also schematically illustrates method action 710 with respect to the presentation level associated with 65 dBHL, where the recipient indicated that the perceived loudness of the hearing percept evoked by that stimulus was loud (4 on the chart). Conversely, the average normal hearing person would have perceived the loudness level of the stimuli (the sound at 65 dBHL) as being of normal loudness. The difference between these two data points is represented by the vertical arrow 820 extending from the empirical data point at 65 dBHL. In an exemplary algorithm, the empirical curve 410 is utilized in method action 710 to obtain a loudness level corresponding to that which the recipient would rate the same as, or at least approximately the same as, that of the normal hearing person. With regard to the exemplary empirical curve 410 of FIG. 8, this corresponds to a loudness level of 62 dBHL, as is represented by the horizontal arrow 822 extending from the aforementioned vertical arrow 820, and the downwardly pointing vertical arrow 824 extending from the horizontal arrow.

Accordingly, in an exemplary embodiment, method action 710 is executed to develop proxy loudness levels based on the statistical data and the empirical data, where the proxy loudness levels correspond to increased levels where the cochlear implant recipient has rated the perceived loudness of a given loudness level as having a rating below that which the normal hearing person would have rated that level, and decreased levels where the cochlear implant recipient has rated the perceived loudness of a given loudness level as having a rating above that which the normal hearing person would have rated that level.

In an exemplary embodiment, the steps of method action 710 can be repeated for each presentation level/loudness level associated with the empirical curve 410. That said, in an alternative embodiment, not all presentation levels/loudness levels are subjected to the steps of method action 710.

Still with reference to FIG. 8A, as seen above, the adjustments to arrive at the given proxy levels are based on the statistical data associated with the average normal hearer (i.e., curve 412). That is, all of the adjustments presented in FIG. 8A are based on moving the perceived loudness to as close to a normalized loudness as possible. That said, in an alternative embodiment, the adjustments to arrive at the given proxy levels can be based on the statistical data associated with the 95 percentile confidence interval (e.g., the area between (and on) curves 414 and 416). In this regard, by way of example only and not by way of limitation, in such an exemplary embodiment, no adjustment would be made with respect to the presentation levels between and including 45 dBHL and 60 dBHL, adjustments with respect to the presentation levels below that range could entail adjustments based on the curve 414, and adjustments with respect to the presentation levels above that range could entail adjustments based on the curve 416. That is, in an exemplary embodiment, the adjustments would be made to simply obtain the proxy levels that fall within the 95$^{th}$ percentile confidence interval. That said, in an alternate embodiment, no adjustments would be made with respect the presentation levels between and including 45 dBHL and 60 dBHL, while adjustments outside of that range could entail adjustments based on the curve 412. That is, in an exemplary embodiment, the adjustments would be made sparingly, but if the adjustments were made, the adjustments would be to drive the resulting loudness to that which corresponds to as close to a normalized loudness as possible. Still further, in at least some exemplary embodiments, presentation levels below the range might be adjusted only to the curve 414, while presentation levels above the range might be adjusted only to the curve 412. Still further, in at least some exemplary embodiments, presentation levels below the range might be adjusted only to the curve 412, while presentation levels above the range might be adjusted only to the curve 416. Other variations are possible in at least some embodiments. Any regime of adjustment based on the statistical data for a normal hearer, whatever the range (50$^{th}$ percentile, 40 to 60 percentile, etc.), can be utilized in at least some embodiments, providing that such has utilitarian value.

Still further, in at least some exemplary embodiments, the resulting proxy levels for values below and/or above a given range can be set such that changes are more gradual than that which would otherwise be the case. By way of example only and not by way of limitation, the first change (e.g., 30 dB HL) can result in a proxy level based on the 95 percentile confidence level (i.e., along curve 414), the second change (e.g., 35 dBHL) can result in a proxy level based on a pseudo-curve is located between the floor of the 95 percentile confidence level and the average (i.e., between curve 414 and curve 412, such as by way of example only and not by way of limitation, ⅓rd of the way between those two curves), the third change (e.g., 40 dBHL) can result in a proxy level based on a pseudo-curve is located between the floor of the 95 percentile confidence level and the average (i.e., between curve 414 and curve 412, such as by way of example only and not by way of limitation, ⅔rds of the way between those two curves), etc. Alternatively and/or in addition to this, a similar but opposite concept can be utilized for the louder values. Alternatively and/or in addition to this, empirically-based step size parameters can be applied so as to smooth the transition between the presentation levels resulting from the adjustments detailed herein. Any algorithm regime that will enable the map changes to be more gradual than that which would be the case, that also have utilitarian value, can in at least some embodiments be utilized.

Still further, it is noted that adjustments to the map changes can be made based on features that are different than those associated with obtaining a gradual increase and/or decrease between presentation levels. By way of example only and not by way of limitation, there may be utilitarian value with respect to providing a limit on upward map adjustments to within a certain safety net. For example, a maximal 10% upward increase might be applied as a limit to ensure that the resulting loudness is not too loud or otherwise results in a safety issue.

FIG. 8B presents an exemplary proxy gain adjustment curve reflecting how the respective presentations levels would be adjusted based on method action 710 to obtain the proxy loudness levels (i.e., the vertical data points on the curve of FIG. 9 correspond to the horizontal arrows of FIG. 8 and the horizontal data points on the curve of FIG. 9 correspond to the respective bases of those arrows).

With reference back to FIG. 7, after method action 710, method action 720 is executed, which entails replacing the respective current levels applied at the respective presentation levels by an amount correlated to the offset data obtained in action 710. In an exemplary embodiment, method action 720 is executed to develop the electrical output function that will result in a hearing percept that is perceived by the recipient is having a loudness that is at least closer to that of a normal hearing person for a given stimuli.

Figure 9A:
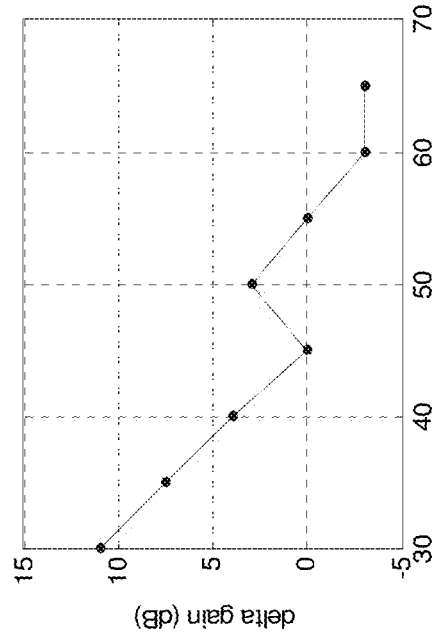
FIGS. 9A, 10A and 11A present composite data pertaining to perceived loudness levels for different presentation levels.
Figure 9B:
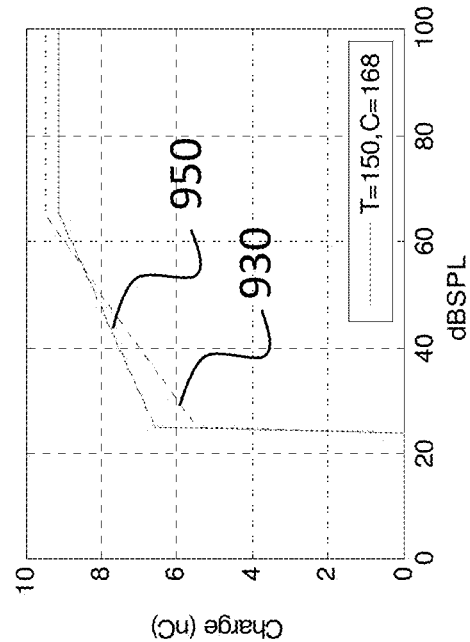
FIGS. 9B, 10B and 11B present exemplary gain change charts for a range of loudness levels in various exemplary scenarios in which the teachings detailed herein are utilized.
Figure 9C:
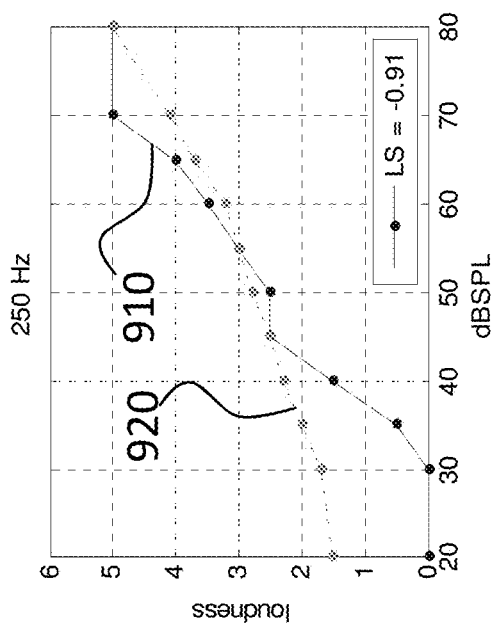
FIGS. 9C, 10C and 11C present exemplary current levels according to exemplary scenarios in which the teachings detailed herein are utilized.

An exemplary method of executing method action 720 will now be described, based on a scaling test for sounds at 250 Hz, where the recipient-specific loudness data and the statistical loudness data has already been obtained. In this regard, FIG. 9A presents a chart detailing the scaling test results for various presentation levels, and the normal hearing statistical data for those same presentation levels (curves 910 and 920, respectively), and FIG. 9B presents a chart detailing the difference between the scaling test results and the normal hearing statistical data for those same presentation levels, where a linear curve fit has been applied for both figures. The curve 910 of FIG. 9A has an average loudness scaling error (LS) of 0.91, relative to the statistical curve 920, averaged over the presentation levels. It is further noted that in an exemplary embodiment, the action of obtaining the recipient specific loudness data further includes the action of obtaining the current regime hearing prosthesis to evoke the hearing percepts associated therewith (e.g., the embryonic map used by the hearing prosthesis to evoke the hearing percepts utilized to develop the scaling test data). FIG. 9C presents that current regime (curve 930). In this regard, the electrode corresponding to the test frequency is determined or otherwise known (hence the current regime for that electrode can be determined). By way of example only, for this test frequency of 250 Hz, utilizing, by way of example, the standard frequency allocation table (or a customized frequency allocation table as the case may be) of a fully functioning 22 contact electrode array of a cochlear implant, the electrodes having a center frequency corresponding best to (e.g., closest to) the tested frequency is identified. It is noted that this can be generalized to other frequency allocation tables, such as by way of example only and not by way of limitation, in the case that some electrodes are disabled for whatever reason. It is further noted that in an exemplary embodiment, the test frequencies can be customized to correspond to a given electrode of the electrode array. That is, empirical data can be utilized to determine the frequency of a given electrode (e.g., electrode X corresponds to 273 Hz), and the tone can be customized to that specific frequency (e.g., to 273 Hz), instead of having to simply use the best (closest) electrode to a test frequency. That said, such might not necessarily be feasible in scenarios where the statistical data is provided for a given specific frequency. That said, in at least some embodiments, some methods entail adjusting the statistical data for one frequency that it is applicable for another frequency. This can be achieved via the utilization of other statistical data that enables such adjustment. Any device, system, and/or method that will enable the correlation between test frequency and a given electrode can be utilized in at least some embodiments.

In an exemplary embodiment, to replace the respective current level applied at the respective presentation levels by an amount correlated to the offset data obtained in action 710, using the obtained current data (e.g., the data represented by curve 930), for each presentation level, the adjustment gain is added to the level in the electrical output is determined for that new game based on the adjustment gain. With respect to FIG. 9C, for the loudness level of 30 dBSPL, the adjustment gain is 11 dB, which results in a proxy loudness level of 41 dBSPL. The corresponding current for that electrode corresponds to approximately 7 nC (as opposed to approximately 6 nC for the current utilized at the loudness level for the scaling test). This is represented by the leftmost "+" symbol. This is now the new current level for the new current regime (the new map) for sounds having a loudness of 30 dBSPL. Again, this process is repeated for each loudness level (35 dBSPL, 40 dBSPL, 45 dBSPL, etc.), although in some alternate embodiments, not all loudness levels are used. The resulting new current levels can be seen by the various "+" symbols on FIG. 9C, where a curve 940 has been superimposed thereon using a curve fitting technique. In this regard, an exemplary embodiment entails utilizing a data manipulation technique, such as by way of example only and not by way of limitation, a curve fitting technique (e.g., linear fitting), to find the optimal threshold level and comfort levels that approximate resulting values, the result being that curves 940 are bounded by new threshold levels and comfort levels. As can be seen, the general trend is that for sounds having a loudness below about 57 dBSPL, the current levels are increase relative to those utilized in the scaling test (those of the first regime), and for sounds having a loudness above about 55 dBSPL, the current levels are decreased relative to those utilized in the scaling test (those of the first regime). Utilizing this new electrical current data, a new current regime (new map) is developed, as represented by curve 950 in FIG. 9D (which also shows curve 930, representing the previous current regime (embryonic map). As can be seen, the portions of the current regime below the loudness levels of the scaling test have been extrapolated utilizing data other than the data associated with the loudness test, and the portions of the current regime above the loudness levels of the scaling test have been truncated at a constant current level. In an exemplary embodiment, these portions of the current regime are developed utilizing standard fitting methods/are developed utilizing standard fitting protocols according to accepted guidelines. By way of example only and not by way of limitation, the current regime of FIG. 9D was developed utilizing a linear alpha model having two degrees of freedom (a threshold value in a comfort value), without limiting at high loudness values and clipping low loudness values.

Figure 9D:
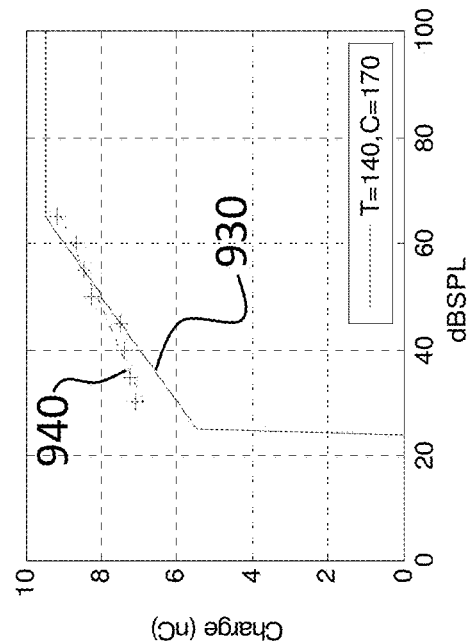
FIGS. 9D, 10D and 11D present exemplary current level functions according to exemplary scenarios in which the teachings detailed herein are utilized.

From FIGS. 9C and 9D, it can be seen that the threshold levels and the comfort levels (T and C levels, respectively) of the two different current regimes are different. Specifically, in the embodiments of FIGS. 9C and 9D, the range between the threshold level and the comfort level is compressed for the new current regime relative to the old current regime. More specifically, FIG. 9C presents a threshold level of 140 (where 140 is a genericized value, as opposed to a nanoCoulomb value) and a comfort level of 170 (again where 170 is a generic sized value). In view current regime, the new threshold level is now 150 and the new comfort level is now 168 (again generic sized values).

In an exemplary embodiment, these new current regimes result in a hearing percept having a normalized loudness, or at least closer to a normalized loudness, with respect to a normal hearing person. That is, in an exemplary embodiment, the electrical stimulation level that is delivered for a given stimulus of a given loudness is that which corresponds to another electrical level (or an extrapolated electrical level associated therewith, more on this below), utilized in another presentation level of the scaling test), where the another electrical level resulted in a hearing percept having a loudness closer to (including the same as), the loudness of a normal hearing person.

It is noted that in an exemplary embodiment, the scaling test provided includes providing sounds having different frequencies. That is, the results of FIGS. 4 and 8A will be present for different frequencies. By way of example only and not by way of limitation, in an exemplary embodiment, a scaling test can encompass 3 different frequencies, such as by way of example only and not by way of limitation, 250 Hz, 1000 Hz and 4000 Hz. The above manipulation steps detailed can be also applied to these different frequencies. In this regard, FIGS. 10A-10D correspond respectively to FIGS. 9A-9D, except for a test frequency of 1000 Hz. Still further in this regard, FIGS. 11A-11D correspond respectively to FIGS. 9A-9D, except for a test frequency of 4000 Hz. As can be seen, in these exemplary examples, the trend is generally the same: a perception of loudness levels lower than the statistical norm at the softer levels, a perception of loudness levels higher than the statistical norm at louder levels, and a shrinking of the threshold levels and the comfort levels at both ends of the loudness spectrum resulting from the new electrical regime (new map), with the most pronounced changes resulting in the low end of the loudness spectrum. That said, these are only exemplary examples. In alternative embodiments, the results could be different. By way of example only and not by way of limitation, the results could be reversed, where the perception of loudness levels for softer levels are higher than the statistical norm, and the perception of loudness levels at the louder levels are lower than the statistical norm and/or the threshold levels and comfort levels could be expanded at both ends, or variations thereof (e.g., the threshold level could be raised at one end and also raised at another end and/or vice versa, the adjustment could result in increased current levels across all of the loudness levels or a decrease in the current levels across all of the loudness levels, an increase in the loudness levels with a decrease in the middle the loudness levels or vice versa etc.).

The above presents some high-level algorithmic details of some embodiments at the macro level. Now, some specific algorithm details will be provided at the micro level. Again, to be clear, all data herein is exemplary, despite the fact that the data is often taken to the fourth decimal place.

The below chart presents a matrix of data associated with exemplary presentation levels of an exemplary scaling test using a sound at 250 Hz, where the columns correspond to the respective presentation levels, and the rows correspond to the loudness level for the given presentation level, the proxy level based on the normal hearing statistical data for the given presentation level, the adjustment to the loudness level to reach the proxy level based on the normal hearing statistical data and the current levels in nanoColoumbs used for each presentation level.

| 30 | 35 | 40 | 45 | 50 | 55 | 60 | 65 |
|---|---|---|---|---|---|---|---|
| 41 | 42.5 | 44 | 45 | 52.996 | 55 | 57 | 62 |
| 11 | 7.5 | 4 | 0 | 2.996 | 0 | −3 | −3 |
| 5.9725 | 6.4719 | 6.9713 | 7.4707 | 7.9701 | 8.4695 | 8.9689 | 9.4683 |

An exemplary algorithm entails using the above data to obtain new current levels that will be used in a new map. By way of example, for each presentation level (stimulus), or a subset thereof, the current levels associated with the actual loudness levels are utilized for the proxy levels that correspond to the actual loudness levels. For example, with respect to the presentation level of 30 dBHL, the proxy level determined based on the statistical data corresponds to 41 dBHL. The current levels associated with the actual loudness level for 41 dBHL are not explicitly known, but the current level for the loudness level of 40 dBHL and the current level for the loudness level of 45 dBHL are known, and these are 6.9713 nC and 7.4707 nC, respectively (i.e., these are the current levels that are utilized to evoke a hearing percept to develop the recipient-specific data from the scaling test). Via linear interpolation (in alternate embodiments, other methods can be used), a current level value is developed for the proxy level of 41 dBHL, which corresponds to 7.07118 nC. This becomes the new current level for the new map for sounds having a loudness of 30 dBHL. Because this current level evokes a hearing percept that is perceived to have a loudness closer to that which would be perceived by the average normal hearing person than that of the old current level (5.9725 nC), the map will provide a more normalized perception of loudness for that specific recipient. This process is repeated for all of the presentation levels, resulting in the following, where the rows correspond to the loudness level for the given presentation level (which will correspond to a future stimuli loudness at which the hearing prosthesis will respond using the new current levels), the proxy level based on the normal hearing statistical data for the given presentation level, the adjustment to the current level to reach the new current level that will evoke a hearing percept that is perceived as being as loud as that perceived by a normal hearing person for that loudness level, and the current levels in nanoCoulombs to be used in the new map when a stimulus having a loudness at the presentation level is applied to the hearing prosthesis in the future (for the electrode corresponding to 250 Hz).

| 30 | 35 | 40 | 45 | 50 | 55 | 60 | 65 |
|---|---|---|---|---|---|---|---|
| 41 | 42.5 | 44 | 45 | 52.996 | 55 | 57 | 62 |
| 0.09988 | 0.2497 | 0.39952 | 0 | 0.29924 | 0 | −0.29964 | −0.29964 |
| 7.07118 | 7.221 | 7.37082 | 7.4707 | 8.26934 | 8.4695 | 8.66926 | 9.16866 |

Accordingly, in an exemplary embodiment, during future use of the hearing prosthesis utilizing the new map, when a sound is captured having a loudness level of, for example, 35 dB at a frequency of 250 Hz, the current applied to the pertinent electrode will be 7.221 nC, and when a sound is captured having a loudness level of, for example, 55 dB, at that same frequency, the current applied to the pertinent electrode will be 8.4695 dB. (Note that these values are values where a linear curve fitting is applied to develop a new current regime utilizing the data above. Other data manipulation methods may result in different current values due to the fact that the data manipulation (e.g. curve fitting techniques) might not necessarily drive the curve through each data point.)

The below chart presents a matrix of data associated with exemplary presentation levels of an exemplary scaling test using a sound at 1000 Hz, where the columns correspond to the respective presentation levels, and the rows correspond to the loudness level for the given presentation level, the proxy level based on the normal hearing statistical data for the given presentation level, the adjustment to the loudness level to reach the proxy level based on the normal hearing statistical data and the current levels in nanoCoulombs used for each presentation level.

| 30 | 35 | 40 | 45 | 50 | 55 | 60 | 65 |
|---|---|---|---|---|---|---|---|
| 39 | 40 | 48 | 45 | 56 | 57 | 58.5 | 59.5 |
| 9 | 5 | 8 | 5 | 5.996 | 1.997 | −1.5015 | −5.5005 |
| 5.9534 | 6.4927 | 7.0319 | 7.5712 | 8.1105 | 8.6498 | 9.189 | 9.7283 |

The above process is repeated for all of the presentation levels, resulting in the following, where the rows correspond to the loudness level for the given presentation level, the proxy level based on the normal hearing statistical data for the given presentation level, the adjustment to the current level to reach the new current level that will evoke a hearing percept that is perceived as being as loud as that perceived by a normal hearing person for that loudness level, and the current levels in nanoCoulombs to be used in the new map (for the electrode corresponding to 250 Hz).

| 30 | 35 | 40 | 45 | 50 | 55 | 60 | 65 |
|---|---|---|---|---|---|---|---|
| 39 | 40 | 47.996 | 45 | 55.996 | 56.997 | 58.4985 | 59.4995 |
| 0.43136 | 0.5392 | 0.862449 | 0.5393 | 0.646729 | 0.215356 | −0.16192 | −0.59328 |
| 6.92406 | 7.0319 | 7.894349 | 8.1105 | 8.757229 | 8.865156 | 9.027078 | 9.135016 |

The below chart presents a matrix of data associated with exemplary presentation levels of an exemplary scaling test using a sound at 4000 Hz, where the columns correspond to the respective presentation levels, and the rows correspond to the loudness level for the given presentation level, the proxy level based on the normal hearing statistical data for the given presentation level, the adjustment to the loudness level to reach the proxy level based on the normal hearing statistical data and the current levels in nanoCoulombs used for each presentation level.

| 30 | 35 | 40 | 45 | 50 | 55 | 60 | 65 |
|---|---|---|---|---|---|---|---|
| 39 | 40 | 40 | 43 | 45 | 46 | 47 | 48 |
| 5.9248 | 6.5323 | 7.1399 | 7.7474 | 8.3549 | 8.9625 | 9.57 | 10.1776 |
| 7.0183 | 7.1399 | 7.1399 | 7.5044 | 7.7474 | 7.8689 | 7.9904 | 8.1119 |

The above process is repeated for all of the presentation levels, resulting in the following, where the rows correspond to the loudness level for the given presentation level, the proxy level based on the normal hearing statistical data for the given presentation level, the adjustment to the current level to reach the new current level that will evoke a hearing percept that is perceived as being as loud as that perceived by a normal hearing person for that loudness level, and the current levels in nanoCoulombs to be used in the new map (for the electrode corresponding to 250 Hz).

| 30 | 35 | 40 | 45 | 50 | 55 | 60 | 65 |
|---|---|---|---|---|---|---|---|
| 39 | 40 | 40 | 45 | 45 | 46 | 47 | 48 |
| 0.48608 | 0.6076 | 0 | −0.243 | −0.6075 | −1.09368 | −1.5795 | −2.06584 |
| 7.01838 | 7.1399 | 7.1399 | 7.5044 | 7.7474 | 7.86882 | 7.9905 | 8.11176 |

Accordingly, in view of the above, the algorithms detailed up to now have enabled the development of data having utilitarian value to normalize loudness hearing percepts relative to a normal hearing person for specific frequencies (the frequencies of the scaling test).

Figure 10A:
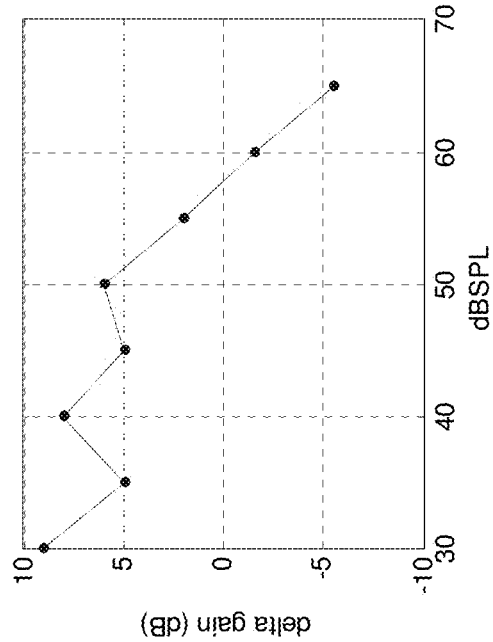
Figure 10B:
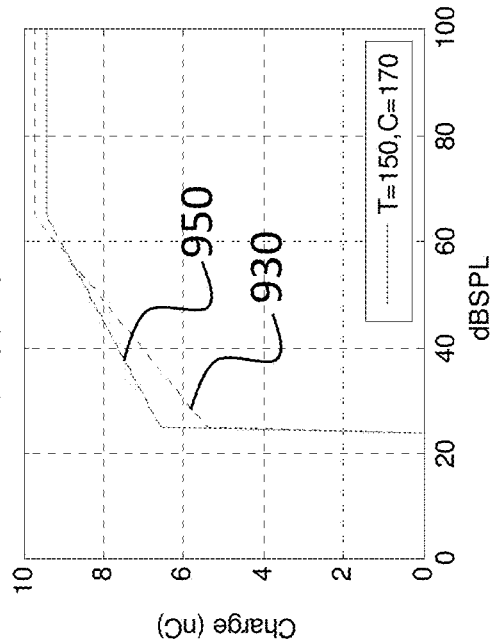
Figure 10C:
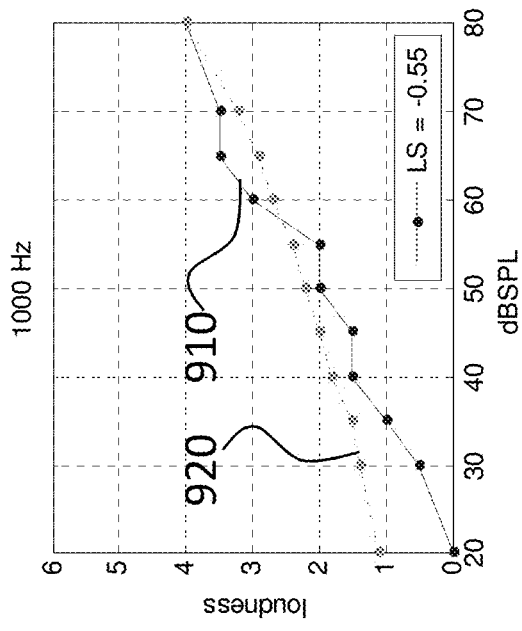
Figure 10D:
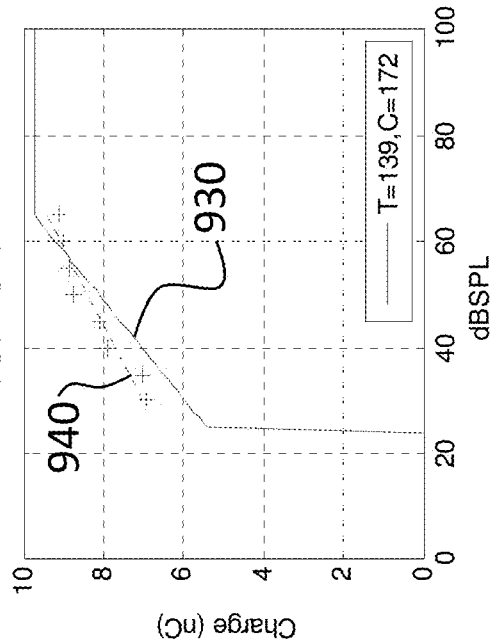
Figure 11A:
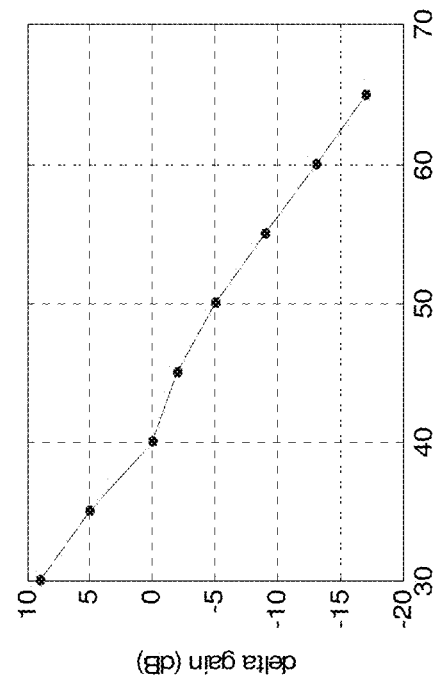
Figure 11B:
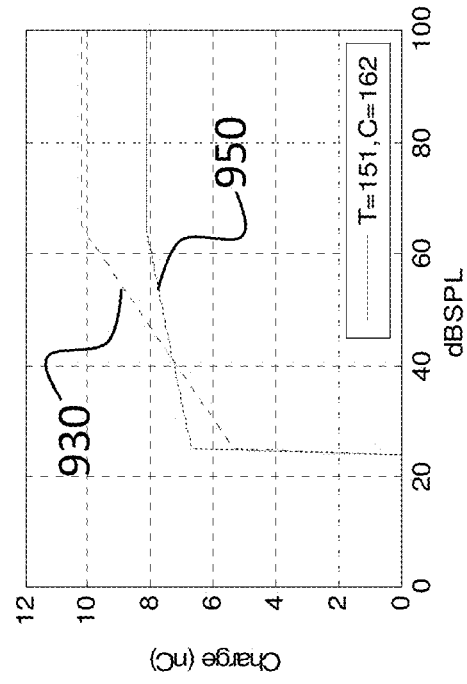
Figure 11C:
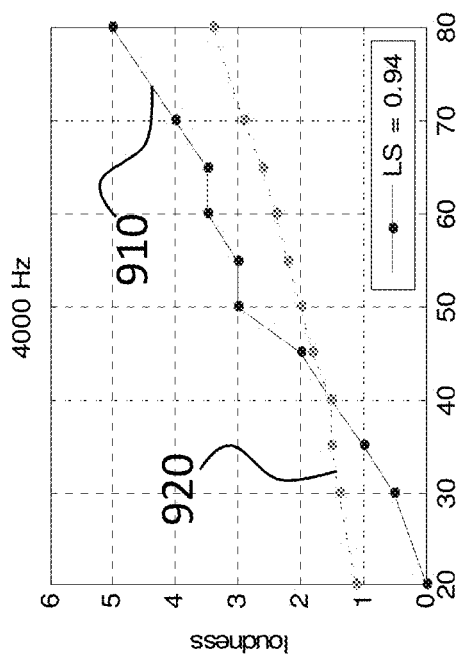
Figure 11D:
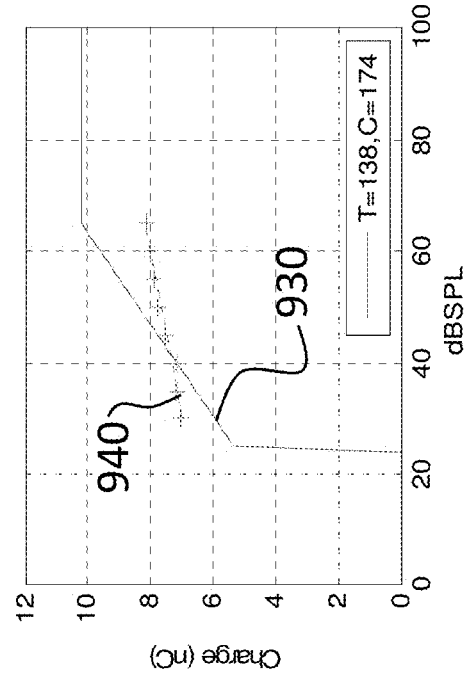

In view of the above, with reference back to the method of flowchart 600 of FIG. 6, in an exemplary embodiment, the action of adjusting at least one of the respective current levels entails increasing the at least one of the respective current levels to an amount that is at least proximate (which includes the same as) the another current level (e.g., as is conceptually represented by the resulting curve 950 relative to the curve 930 of FIGS. 9D, 10D and 11D). As used herein, the phrase "proximate another current level" includes any current level that results in a perceived loudness that is closer to a normalized loudness than that which would be the case without the teachings detailed herein. Also, as will be understood from the above, the action of adjusting at least one of the respective current levels can entail increasing the at least one of the respective current levels to an amount that is at least one of at or is an extrapolated value from the another current level (e.g., resulting in the lower loudness level portions of the curve 950 relative to the curve 930).

In an exemplary embodiment, the action of creating the map for the hearing prosthesis entails creating the map based on the obtained data by adjusting at least one other of the respective current levels based on data of a respective perceived loudness for another current level different from that upon which the at least one of the respective current levels was adjusted. An exemplary method further includes adjusting the at least one other of the respective current levels by decreasing the at least one other of the respective current levels to an amount that is at least one of at or is an extrapolated value from the another current level different from that upon which the at least one of the respective current levels was adjusted (e.g., resulting in the higher loudness level portions of the curve 950 relative to the curve 930).

Still further, in view of the above, again with continuing reference to the method associated with FIG. 6, the action of adjusting at least one of the respective current levels entails identifying a respective perceived loudness for the another current level based on a correlation with the statistical data. This is generally represented conceptually by FIG. 8A in combination with FIGS. 9D, 10D and 11D.

Corollary to the above is that in at least some exemplary embodiments, the different current levels of the plurality of hearing percepts are correlated to respective different loudness levels of respective different noise stimuli, wherein higher loudness level is directly correlated with higher current level. This is seen in FIGS. 9C, 10C, and 11C. Still further, the action of adjusting at least one of the respective current levels entails identifying the respective perceived loudness for the another current level that corresponds to a normalized loudness for the respective different noise stimulus and using the another current level to develop adjustment data to adjust the at least one of the respective current levels. This is generally conceptually represented by FIG. 8A in combination with FIGS. 9B, 9C, 10B, 10C, 11B and 11C.

Figure 12:
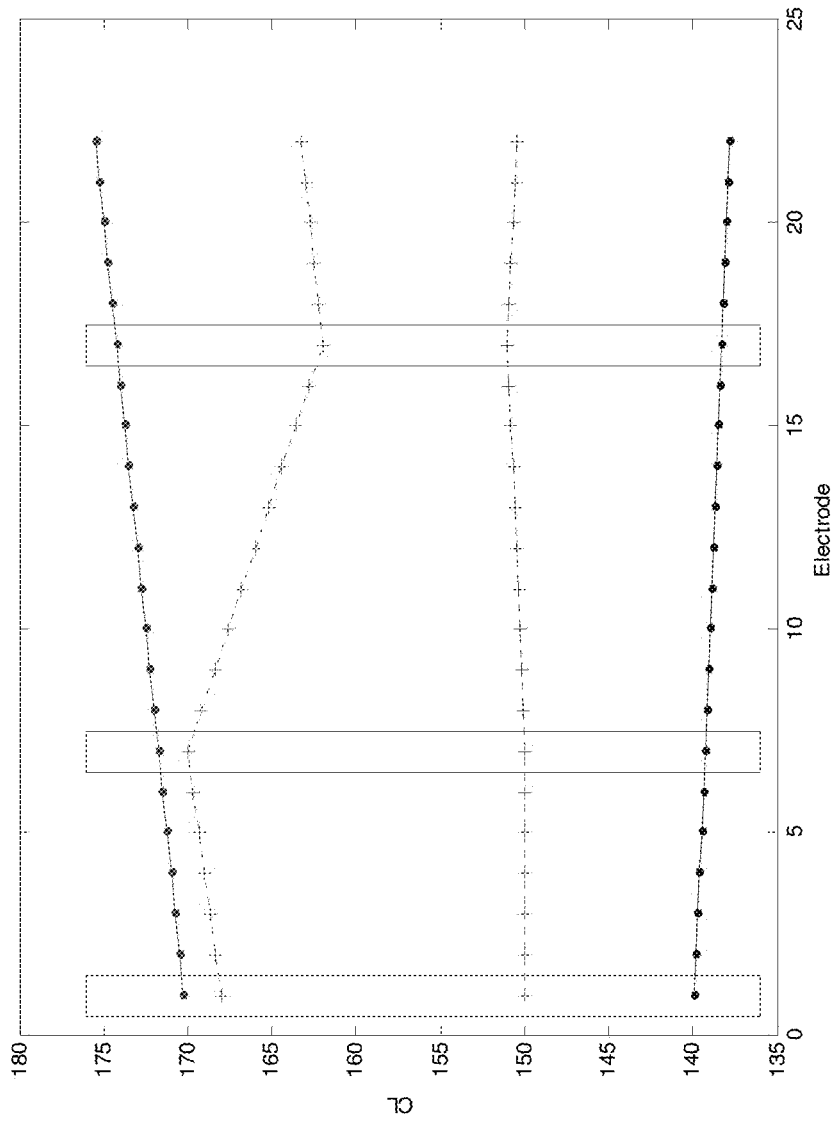
FIG. 12 presents exemplary threshold level and comfort level curves for exemplary scenarios in which the teachings detailed herein are utilized.

Some exemplary embodiments further include methods of developing the different current regimes to normalize loudness for frequencies different than those utilized in the scaling test. That is, in an exemplary embodiment, not all frequencies will be utilized as test frequencies in the loudness scaling test. Thus, in an exemplary embodiment, to complete a map adjustment for monopolar maps, interpolation can be utilized. In this regard, in an exemplary embodiment, utilizing the three test frequencies and the map adjustments developed above (where, in some exemplary embodiments, data manipulation techniques, such as curve fitting techniques, are applied to develop a regime that addresses not only loudness levels corresponding to the specific presentation levels, but also to the levels in between), the other electric parameters can be linearly interpolated. In this regard, FIG. 12 depicts a series of curves presenting genericized current levels relative to electrode number for the original map (original current regime) utilized to evoke a hearing percepts in the scaling test (the dotted solid lines), with the electrode numbers corresponding to those related to the frequencies of the three frequency tests administered above encased in the 3 respective boxes (electrode 1 corresponding to 250 Hz, electrode 7 corresponding to 1000 Hz, and electrode 17 corresponding to 4000 Hz). The top two curves correspond to comfort level curves and the bottom two curves correspond to threshold level curves.

In at least some exemplary embodiments, the current level value for each of the electrodes for the original current level regime (the original map) utilized to evoke a hearing percept during scaling test is known. In this regard, each dot represents the exact portion of the map utilized during the scaling test. Superimposed onto FIG. 12 are the current levels corresponding to the adjusted current levels resulting from the above algorithms. These are located within the boxes encasing electrodes 1, 7, and 17, represented by the "+" symbol. In the exemplary embodiment presented in FIG. 12, linear interpolation has been utilized to develop data for each of the electrodes in between the electrodes corresponding to the frequencies utilized during the scaling test. Again, in some other embodiments, other types of data manipulation/data management can be utilized. That is, linear interpolation is one of the various ways to develop the data for the non-presentation frequencies.

In at least some exemplary embodiments, for frequencies above highest frequencies utilized during the scaling test (e.g., 4000 Hz), the adjustment for the highest frequency (e.g., 4000 Hz) is utilized. That said, in an alternate embodiment, the values can be extrapolated using any applicable data manipulation technique that can have utilitarian value (e.g., linear extrapolation).

Figure 13:
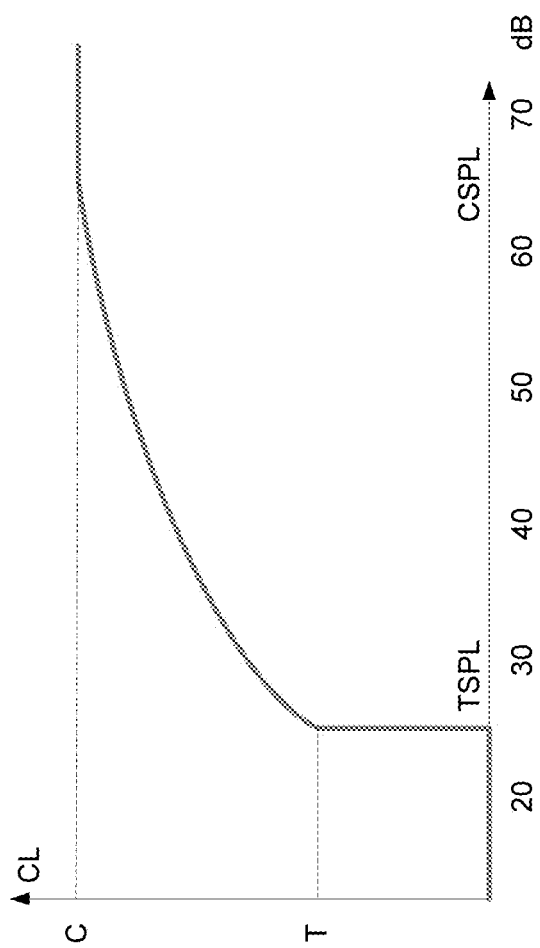
FIG. 13 presents an exemplary function having utilitarian value in some exemplary embodiments of the teachings detailed herein.

Accordingly, in an exemplary embodiment, a new map can be developed having threshold levels and comfort levels corresponding to those of a normal hearing person for a given set of stimuli. In some exemplary embodiments, standard electrical output functions of known utilitarian value can be utilized to develop the current regime between the threshold levels and comfort levels, at least for the electrodes other than those utilized for the scaling test (although, in an alternate embodiment, the empirical data for those tests can also be substituted by these standard electrical output function for consistency). By way of example only and not by way of limitation, FIG. 13 presents an exemplary function that can be used to fill in the data in between the threshold level (TSPL) and the comfort level (CSPL). That is, the current level for the threshold level and the current level for the comfort level in the superimposed onto the graph of FIG. 13 at the T position and the C position, respectively, and the current levels for loudness is there between can be developed following the curve between those two positions.

In an alternate embodiment, the current regime for the non-test electrodes for loudness levels in between the threshold level and/or comfort level can be developed utilizing data manipulation based on the empirical results from those loudness levels from the scaling test. Again, in at least some exemplary embodiments, linear interpolation can be utilized from the empirical test results for those in between loudness levels for the known test electrodes to develop current regimes for the non-test electrodes.

Accordingly, in at least some exemplary embodiments detailed herein, a new map can be developed that better approximates normal hearing loudness. This new electrical map can then be approximated within the parameters space of the exposed clinical parameters. In at least some exemplary embodiments of the algorithms detailed herein, the algorithm results in a proportional relationship between the parameters. For example, small deviations from the normal hearing regime will result in small map changes, while large deviations from the normal hearing regime will result in large map changes, at least in some exemplary embodiments.

Figure 14:
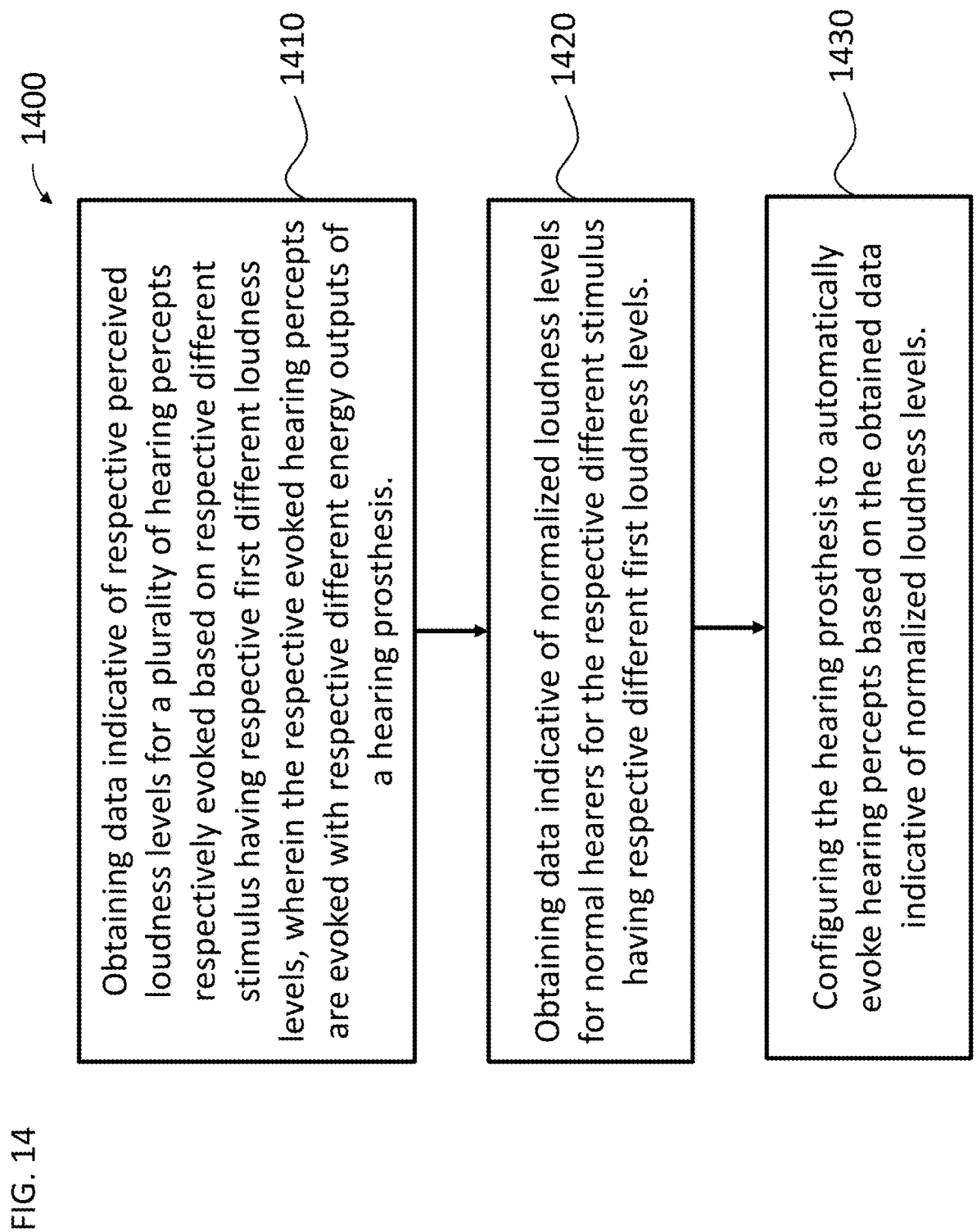
FIG. 14 presents a flowchart for another exemplary method according to another exemplary embodiment.

Now, with reference to FIG. 14, another exemplary method will be described. FIG. 14 presents a flowchart 1400, which includes method action 1410, which entails obtaining data indicative of respective perceived loudness levels for a plurality of hearing percepts respectively evoked based on respective different stimulus having respective first different loudness levels, wherein the respective evoked hearing percepts are evoked with respective different energy outputs of a hearing prosthesis. This is conceptually represented by curve 410 of FIG. 4, curve 910 of FIG. 9A, and curve 930 of FIG. 9C. Flowchart 1400 further includes method action 1420, which entails obtaining data indicative of normalized loudness levels for normal hearers for the respective different stimulus having respective different first loudness levels. This is represented by curve 412 of FIG. 4 and curve 920 of FIG. 9A.

Flowchart 1400 further includes method action 1430, which entails configuring the hearing prosthesis to automatically evoke hearing percepts, in response to sound captured by the hearing prosthesis having respective second different loudness levels corresponding to the respective first different loudness levels, at respective new different energy levels different from those used to evoke the respective hearing percepts, for respective new respective stimulus having the respective first different loudness levels, based on the obtained data indicative of normalized loudness levels. This is conceptually represented by loading a map into the hearing prosthesis having an electrical current regime based on curves 950 of FIGS. 9D, 10D and 11D. In a similar vein, in an exemplary embodiment, the action of configuring the hearing prosthesis entails setting a map of the hearing prosthesis to automatically evoke the hearing percepts at respective energy levels in response to sound captured by the hearing prosthesis having, relative to the respective current levels, respective loudness levels corresponding to those of the respective different stimulus based on the obtained data.

In at least some exemplary embodiments, the action of obtaining data indicative of respective perceived loudness levels entails obtaining empirical perceived loudness data for a plurality of different presentation levels of a loudness test administered to a recipient of the hearing prosthesis. This is conceptually represented by FIGS. 4 and 8 as detailed above.

In an exemplary embodiment of the method represented by FIG. 14, there is a variation of that method which entails developing (which includes simply obtaining from another source) a first current level regime in which respective loudness levels of the respective different stimulus are correlated with respective current levels of an electrode array of the hearing prosthesis. This is conceptually represented by obtaining the curves 930 of FIGS. 9C, 10C and 11C. This variation of the method can further entail developing a second current level regime in which respective loudness levels of future sounds captured by the hearing prosthesis are correlated with respective future current levels of the electrode array. This is conceptually represented by obtaining the curves 950 of FIGS. 9D, 10D and 11D. This variation of the method can further result in the action of configuring the hearing prosthesis to automatically evoke hearing percepts at respective energy levels such that the hearing prosthesis is configured to automatically evoke hearing percepts according to the second current level regime instead of the first current level regime. Again, in an exemplary embodiment, such can be achieved by developing a map based on the curves 950 of FIGS. 9D, 10D and 11D, and loading that map into the hearing prosthesis such that the hearing prosthesis will evoke a hearing percept based on that map.

Corollary to the above is that, in at least some exemplary embodiments, the action of developing the second current regime entails adjusting the respective current levels of the first regime to those of the second regime for respective loudness levels of the different stimulus and future sounds that are the same, based on values of the current level of the first regime and the obtained data indicative of normalized loudness levels for normal hearers, wherein the obtained data indicative of normalized loudness levels is statistical data. This is conceptually represented by FIGS. 9C, 10C and 11C and FIGS. 9D, 10D and 11D.

Along these lines, in an exemplary embodiment of the method of FIG. 14, the method results in a scenario where the action of configuring the hearing prosthesis results in the hearing prosthesis automatically evoking hearing percepts that have loudness percepts closer to those of the normalized loudness levels for the respective different stimulus relative to that which is the case for the obtained data indicative of the respective perceived loudness levels. This is conceptually represented by FIG. 8A above.

With reference back to FIG. 12, it can be understood that in at least some exemplary embodiments, the method of FIG. 14 can further comprise obtaining second data indicative of respective perceived loudness levels for a plurality of hearing percepts respectively evoked based on respective different stimulus at a second frequency having respective first different loudness levels, wherein the respective evoked hearing percepts are evoked with the respective different energy outputs of a hearing prosthesis. This is conceptually represented by curve 910 of FIG. 10A (or 11A), and curve 930 of FIG. 10C (or 11C). An exemplary method can further entail obtaining second data indicative of normalized loudness levels for normal hearers for the respective different stimulus at the second frequency having the respective different first loudness levels. This is conceptually represented by curve 920 of FIG. 10A (or 11A). The currently discussed exemplary method can further entail configuring the hearing prosthesis to automatically evoke hearing percepts, in response to sound at the second frequency captured by the hearing prosthesis having the respective second different loudness levels corresponding to the respective first different loudness levels, at respective new second different energy levels different from those used to evoke the respective hearing percepts based on respective different stimulus at the second frequency, for respective new respective stimulus having the respective first different loudness levels and the second frequency, based on the obtained data indicative of normalized loudness levels for the second frequency. This is conceptually represented by following the procedure detailed above with respect to FIG. 12 to develop a map based on the electrical current regimes based on curves 950 of FIG. 10D in combination with data based on curves 950 of FIGS. 9D, and/or 11D. As will be readily apparent from the teachings detailed above, in at least some examples of this exemplary method, at least some of the respective new different energy levels will be different than at least some of the respective second new different energy levels for respective first different loudness levels.

The teachings detailed herein and/or variations thereof are applicable to both cochlear implants, and other types of hearing prostheses that utilize a gain function. In this regard, by way of example, not only are the teachings detailed herein applicable to a cochlear implant, in at least some embodiments, the teachings detailed herein are applicable to a bone conduction device and/or a middle ear implant. Still further, the adjusted values detailed herein can be applied directly in the acoustic channels of a hybrid device and/or a wide dynamic range compression hearing aid. Accordingly, in an exemplary embodiment, there is a method of fitting such devices utilizing one or more or all of the method actions detailed herein. Still further, in an exemplary embodiment, there are such devices fitted to a recipient by executing one or more or all the method actions detailed herein.

In general terms, an exemplary embodiment entails the development of a map that results in the control of the amplification (e.g., gain) of the hearing prosthesis (or some other parameter and/or parameters) that results in a hearing percept such that the resulting hearing percept for a given stimulus and/or for a range of stimuli has a perceived loudness that is at least similar to (or at least closer to), if not identical to, a loudness perceived for the given stimulus/range of stimuli by a normal hearing person. Also in general terms, the developed map can result in the control of one or more various parameters that in turn results in a hearing percept, wherein the resulting hearing percept for a given stimulus and/or for a range of stimuli has a perceived loudness that is at least closer to a loudness perceived for the given stimuli/range of stimulus by a normal hearing person relative to that which is (was) the case without the control.

In general terms, in an exemplary embodiment, there is a method of using a three-step algorithm (no additional steps are needed in some embodiment) to tune map parameters of a frequency channel. Loudness ratings resulting from the hearing prosthesis recipient based on hearing percepts utilizing an initial map can be utilized to generate a new map.

In at least some embodiments, a model of the electrical output function of a given hearing prosthesis as initially set is utilized to develop an initial dataset relating to perceived loudness, and this initial dataset is utilized to develop a new electrical output function by comparing the data set to statistical values relating to loudness. An exemplary method estimates adjustment gains that can be utilitarianly made to adjust the map such that the adjusted map (new map) results in the hearing percept having loudness values more closely approximating (if not generally identical to) a normal hearing person.

Moreover, an exemplary embodiment entails utilizing the same approaches as detailed herein (e.g., the same algorithms detailed herein), to normalize both electrical hearing and acoustical hearing parameters. Accordingly, an exemplary embodiment entails fitting an electrical hearing device and an acoustic hearing device utilizing the same algorithm according to the teachings detailed herein, at least to normalize loudness. Again, this can be applicable to a hybrid system (where the cochlear implant and acoustical device are utilized in the same ear) or a contralateral system (a bimodal system, where one side utilizes an electrical hearing device and the other utilizes another type of hearing device, such as an acoustic hearing device). Accordingly, an exemplary embodiment entails utilizing the same approaches as detailed herein (e.g., the same algorithms detailed herein) to normalize the hearing parameters of both of the components of a hybrid system and/or a contralateral system. Accordingly, an exemplary embodiment entails fitting a hybrid system and/or a contralateral system utilizing the same algorithm according to the teachings detailed herein, at least to normalize loudness.

In keeping with the above, in an exemplary embodiment, the methods detailed herein can be utilized to instead develop a compression regime adjustment regime of a hearing prosthesis. That is, in an exemplary embodiment, the map of the hearing prosthesis is not necessarily changed (e.g., the map utilized to implement the scaling test is not changed/the hearing prosthesis maintains that map after the methods detailed herein are implemented). Instead, a block is built into the hearing prosthesis that gives varying additional amplification per channel that is correlated to the loudness of various sound captured by the hearing prosthesis. Any device, system, and/or method that can implement the teachings detailed herein, such that the resulting hearing percept is normalized, can be utilized in at least some embodiments.

It is noted that while the teachings detailed herein are described in terms of an electrical stimulating device in the form of a cochlear implant, it is noted that alternate embodiments are applicable to other types of stimulating devices. By way of example only and not by way of limitation, the teachings detailed herein and/or variations thereof can be applicable to a bone conduction device, a Direct Acoustic Cochlear Implant, or traditional hearing aids, at least those having channel features. Indeed, in the embodiments where there are no specifically divided channels, proxy channels can be established. That is, the frequency spectrum can be divided into frequency bands for data manipulation purposes, and the respective frequency bands can be treated as channel.

As noted above, at least some of the method actions can be executed at a location remote from where another method action is located. For example, it is noted that an exemplary embodiment entails executing some or all of the method actions detailed herein, where the recipient of the hearing prosthesis is located remotely (e.g., geographically distant) from where at least some of the method actions detailed herein are executed (e.g., any method action detailed herein that can be executed by, for example, a computer or other processor located at a remote location). For example, any of the methods detailed herein could be executed via internet communication with the hearing prosthesis and the user interface 314 and/or the hearing implant fitting system 306 (e.g., communication link 308 of FIG. 3 can be an internet connection or a wired or wireless connection). Still further by example, with respect to a given method, one or more method actions can be executed at one location (controlled by the audiologist 304 at another location geographically remote from the one location), and one or more other method actions can be executed at the location where the audiologist 304 is located. That is, any method action herein can be executed at one location, and any method action herein can be executed at another location, and so on, providing that the teachings detailed herein and/or variations thereof can be practiced.

It is further noted that in an alternate embodiment, one or more of the method actions detailed herein are executed by the recipient of the cochlear implant. Indeed, in an exemplary embodiment, there is a system that enables a recipient to execute, in conjunction with the system, the method actions detailed herein such that the cochlear implant can be remapped without any additional input from a clinician or the like.

It is noted that any disclosure of a method action detailed herein corresponds to a disclosure of a corresponding system and/or device for executing that method action, in at least some embodiments, automatically. It is further noted that any disclosure of an apparatus or system herein corresponds to a disclosure of a method of operating that apparatus. It is also noted that any disclosure of any method action detailed herein further includes a disclosure of executing that method action in an automated fashion, as well as a device for executing those method actions in the automated manner.

It is further noted that any disclosure of a fitting method herein corresponds to a hearing prosthesis or hearing device fitted according to that method.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. A method, comprising:
obtaining data indicative of respective perceived loudnesses for a plurality of hearing percepts respectively evoked based on different stimulation signals of a hearing device;
creating a program for the hearing device based on the obtained data by adjusting at least one of the respective stimulation signals based on data of a respective perceived loudness for other stimulation signals; and
configuring the hearing device to have the created program, wherein
the action of obtaining data includes obtaining a loudness scaling test dataset.

2. The method of claim 1, wherein:
the action of adjusting at least one of the respective stimulation signals includes increasing one or more current levels of the stimulation signals to an amount that is at least proximate to another current level of the stimulation signals.

3. The method of claim 1, wherein:
the action of adjusting at least one of the respective stimulation signals includes increasing one or more current levels of the stimulation signals to an amount that is at least one of at another current level of the stimulation signals or at an extrapolated value from the another current level.

4. The method of claim 1, wherein:
the action of adjusting at least one of the respective stimulation signals includes adjusting the at least one of the respective stimulation signals based on statistical data.

5. The method of claim 4, wherein:
the action of adjusting at least one of the respective stimulation signals includes identifying a respective perceived loudness for the other stimulation signals based on a correlation with the statistical data.

6. The method of claim 1, wherein:
the different stimulation signals of the plurality of hearing percepts are correlated to respective different loudness levels of respective different noise stimulus, wherein higher loudness level is directly correlated with higher current level used with the stimulation signals, and
the action of adjusting at least one of the respective stimulation signals includes identifying the respective perceived loudness for the other stimulation signals that corresponds to a statistically based loudness for the respective different noise stimulus and using the other stimulation signals to develop adjustment data to adjust the at least one of the respective stimulation signals.

7. A method, comprising, in a same fitting session of a single recipient:
obtaining data indicative of respective perceived sensory levels for a plurality of sensory percepts respectively evoked based on respective different stimulus having respective first different stimulus levels, wherein the respective evoked sensory percepts are evoked with respective different energy outputs of a sensory device;
obtaining data indicative of statistical stimulus levels for a statistically significant population for the respective different stimulus having respective different first stimulus levels;
configuring the sensory device to automatically evoke sensory percepts, in response to sound captured by the sensory device having respective second different stimulus levels corresponding to the respective first different stimulus levels, at respective new different energy levels different from those used to evoke the respective sensory percepts, for respective new respective stimulus having the respective first different stimulus levels, based on the obtained data indicative of statistical stimulus levels;
obtaining second data indicative of respective second perceived stimulus levels for a second plurality of sensory percepts respectively evoked based on respective second different stimulus having respective third different stimulus levels, wherein the respective second evoked sensory percepts are evoked with respective second different energy outputs of the sensory device;
obtaining second data indicative of statistical stimulus levels for the statistically significant population for the respective second different stimulus having respective different third stimulus levels; and
configuring the sensory device to automatically evoke sensory percepts, in response to stimulus captured by the sensory device having respective fourth different stimulus levels corresponding to the respective third different stimulus levels, at respective second new different energy levels different from those used to evoke the respective second sensory percepts, for respective second new respective stimulus having the respective third different stimulus levels, based on the obtained second data indicative of statistical stimulus levels.

8. The method of claim 7, wherein:
the action of configuring the hearing device includes setting a program of the hearing device to evoke the sensory percepts at respective energy levels in response to sound captured by the sensory device having, relative to the respective energy levels, respective stimulus levels corresponding to those of the respective different stimulus based on the obtained data.

9. The method of claim 7, wherein:
the action of configuring the sensory device results in the sensory device automatically evoking sensory percepts that have stimulus percepts closer to those of the statistical stimulus levels for the respective different stimulus relative to that which is the case for the obtained data indicative of the respective perceived stimulus levels.

10. A fitting system, comprising:
a sub-system configured to obtain statistical perceived loudness data;
a sub-system configured to obtain hearing device recipient-specific loudness data for a plurality of different stimulus having at least some loudness levels corresponding to those of the statistical perceived loudness data; and
a sub-system configured to configure a hearing device based on the obtained statistical data and the obtained recipient-specific loudness data, wherein
the fitting system is configured to configure the hearing device based on the obtained statistical data and the obtained recipient-specific loudness data by adjusting an output energy level of the hearing device based on a respective recipient-specific loudness data for another output energy level, wherein the adjusted output energy level is at or proximate the another output energy level.

11. The system of claim 10, wherein:
the obtained recipient-specific loudness data is generated using the hearing device to evoke a plurality of hearing percepts using a first program;
the sub-system configured to automatically determine respective offsets between the recipient-specific loudness data and the statistical perceived loudness data for the respective plurality of different stimulus having the at least some loudness levels corresponding to those of the statistical perceived loudness levels; and
the sub-system is configured to automatically use the offsets to automatically adjust the first program and create a second program based on the adjustment; and
the sub-system configured to automatically configure the hearing device configures the hearing device by loading the second program into the hearing device.

12. The system of claim 10, wherein:
the at least some loudness levels corresponding to those of the statistical perceived loudness data includes at least some loudness levels that are either at or proximate to the statistical perceived loudness data.

13. The system of claim 10, wherein:
the action of configuring the hearing device includes adjusting a current level regime of the hearing device such that applied stimulation signals at the current levels of the current level regime at least results in a perceived loudness that at least approximately corresponds to those of the statistical perceived loudness for a given stimulus.

14. The system of claim 10, wherein:
the sub-system configured to configure the hearing device based on the obtained statistical data and the obtained recipient-specific loudness data is configured to automatically configure the sub-system configured to configure the hearing device based on the obtained statistical data and the obtained recipient-specific loudness data.

15. The method of claim 7, wherein:
the action of obtaining data indicative of respective perceived stimulus levels includes obtaining empirical perceived stimulus data for a plurality of different presentation levels of a stimulus test administered to a recipient of the sensory device.

16. The method of claim 7, wherein:
at least some of the respective new different energy levels are different than at least some of the respective second new different energy levels for respective first different loudness levels.

17. A method, comprising:
obtaining data indicative of respective perceived loudnesses for a plurality of sensory percepts respectively evoked based on different electrical stimulation signals of a sensory stimulator sensory stimulator;
creating a program for the sensory stimulator based on the obtained data by adjusting at least one of the respective electrical stimulation signals based on data of a respective perceived loudness for other electrical stimulation signals; and
configuring the sensory stimulator to have the created program, wherein
at least one of:
the action of creating a program includes adjusting a loudness scaling test dataset based on statistical data;
the method further includes identifying electrical stimulation signal(s) corresponding to a threshold level for a recipient of the sensory stimulator;
the different electrical stimulation signals are based on sound captured by a microphone of the sensory stimulator;
the method further includes identifying electrical stimulation signal(s) corresponding to a comfort level for the recipient; or
the adjustment of the at least one of the respective electrical stimulation signals results in a plurality of different current levels located between a current level used with the electrical stimulation signals corresponding to the threshold level and a current level used with the electrical stimulation signals corresponding to the comfort level.

18. The method of claim 17, further comprising:
identifying the electrical stimulation signal(s) corresponding to the threshold level for the recipient of the sensory stimulator; and
identifying the electrical stimulation signal(s) corresponding to the comfort level for the recipient, wherein
the adjustment of the at least one of the respective electrical stimulation signals results in the plurality of different current levels located between the current level corresponding to the threshold level and the current level corresponding to the comfort level.

19. The method of claim 17, wherein:
the action of obtaining data includes obtaining the loudness scaling test dataset; and
the action of creating the program includes adjusting the loudness scaling test dataset based on statistical data.

20. The method of claim 17, wherein:
the adjustment of the at least one of the respective electrical stimulation signals results in a plurality of different current levels located between a current level used with the electrical stimulation signals corresponding to the threshold level and a current level used with the electrical stimulation signals corresponding to the comfort level.

21. The method of claim 1, wherein:
the hearing device is or has functionality of an electrical hearing device and/or an acoustic hearing device.

22. The system of claim 10, wherein:
the fitting system is configured to be remote from the hearing device when configuring the hearing device.

23. The system of claim 10, wherein:
the fitting system includes different respective statistical perceived loudness data for different respective populations.

24. The system of claim 10, wherein:
the fitting system includes different respective statistical perceived loudness data with different respective confidence margins, and enables a user to select a given respective statistical perceived loudness data from the different respective statistical perceived loudness data.

25. The system of claim 10, wherein:
the fitting system is configured to develop proxy loudness levels based on the statistical data and the recipient-specific loudness data, where the proxy loudness levels correspond to increased levels where the recipient has rated the perceived loudness of a first given loudness level as having a rating below that which a statistically based hearing person would have rated that first given loudness level, and decreased levels where the recipient has rated a perceived loudness of a second given loudness level as having a rating above that which the statistically based hearing person would have rated that second given loudness level.

26. The method of claim 7, wherein:
the sensory percepts are hearing percepts; and
the sensory device is a hearing device, and the stimulus levels are loudness levels.

* * * * *